(12) United States Patent
Miura et al.

(10) Patent No.: US 8,344,095 B2
(45) Date of Patent: Jan. 1, 2013

(54) FUSED RING COMPOUND, METHOD FOR PRODUCING THE SAME, POLYMER, ORGANIC THIN FILM CONTAINING THE COMPOUND AND/OR POLYMER, AND ORGANIC THIN FILM DEVICE AND ORGANIC THIN FILM TRANSISTOR EACH COMPRISING THE ORGANIC THIN FILM

(75) Inventors: Masahiro Miura, Suita (JP); Tetsuya Satoh, Suita (JP); Hayato Tsurugi, Suita (JP); Jun Kumagai, Suita (JP); Masato Ueda, Tsukuba (JP)

(73) Assignees: Osaka University, Osaka (JP); Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/867,182
(22) PCT Filed: Feb. 12, 2009
(86) PCT No.: PCT/JP2009/052319
§ 371 (c)(1),
(2), (4) Date: Oct. 18, 2010
(87) PCT Pub. No.: WO2009/101982
PCT Pub. Date: Aug. 20, 2009

(65) Prior Publication Data
US 2011/0065895 A1 Mar. 17, 2011
US 2011/0213119 A2 Sep. 1, 2011

(30) Foreign Application Priority Data
Feb. 13, 2008 (JP) ................................. 2008-032246

(51) Int. Cl.
*C08G 75/00* (2006.01)
(52) U.S. Cl. ........................................ 528/377; 528/380
(58) Field of Classification Search .................. 528/377, 528/380
See application file for complete search history.

(56) References Cited

U.S. PATENT DOCUMENTS
5,843,607 A * 12/1998 Hu et al. ...................... 430/58.5
(Continued)

FOREIGN PATENT DOCUMENTS
JP           5-110069 A      4/1993
(Continued)

OTHER PUBLICATIONS

Zhenan Bao, et al.,"Soluble and processable regioregular poly(3-hexylthiophene) for thin film filed-effect transistor applications with high mobility", Appl. Phys. Lett., Dec. 1996, pp. 4108-4110.
(Continued)

*Primary Examiner* — Shane Fang
(74) *Attorney, Agent, or Firm* — Sughrue Mion, PLLC

(57) ABSTRACT

An object of the present invention is to provide a fused ring compound which can show sufficient charge transport properties and also has excellent solubility in a solvent. The fused ring compound of the present invention is represented by the following formula (1):

[Chemical Formula 1]

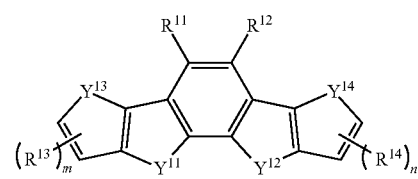

(1)

wherein $R^{11}$ and $R^{12}$ each independently represent a hydrogen atom, an alkyl group, an alkoxy group, an alkylthio group, an alkylamino group, an alkoxycarbonyl group having 3 or more carbon atoms in the alkyl moiety thereof, an aryl group which may have a substituent, a monovalent heterocyclic group which may have a substituent, or a cyano group, wherein at least one of $R^{11}$ and $R^{12}$ is not a hydrogen atom; $R^{13}$ and $R^{14}$ each independently represent a monovalent group and m and n are an integer of 0 to 2; $Y^{11}$, $Y^{12}$, $Y^{13}$ and $Y^{14}$ are a predetermined divalent group containing S, O, N, Se, Te or a double bond; $Y^{11}$ and $Y^{12}$ are selected so that a ring containing the groups forms a five-membered ring; and $Y^{13}$ and $Y^{14}$ are selected so that a ring containing the groups forms a five or six-membered ring.

9 Claims, 11 Drawing Sheets

U.S. PATENT DOCUMENTS

| | | | |
|---|---|---|---|
| 2009/0065770 A1 | 3/2009 | Miura et al. | |
| 2009/0156832 A1 | 6/2009 | Miura et al. | |
| 2009/0302743 A1* | 12/2009 | Kato et al. | 313/504 |
| 2009/0309488 A1* | 12/2009 | Kato et al. | 313/504 |
| 2011/0060097 A1* | 3/2011 | Wang | 524/548 |

FOREIGN PATENT DOCUMENTS

| | | |
|---|---|---|
| JP | 2001-508023 A | 6/2001 |
| JP | 2004-006476 A | 1/2004 |
| JP | 2004-339516 A | 12/2004 |
| JP | 2008-010541 A | 1/2008 |
| WO | 2005/087780 A1 | 9/2005 |
| WO | 2007/105386 A1 | 9/2007 |

OTHER PUBLICATIONS

Robert L. Hudkins, et al., "Synthesis and Mixed Lineage Kinase Activity of Pyrrolocarbazole and Isoindolene Analogs of (+)K-252a", Journal of Medicinal Chemistry, 2007, pp. 433-441, vol. 50, No. 3.

Uwe Dahlmann, et al., "The Diyne Reaction of 3.3'-Bis(phenylethynyl)-2,2'-Bithiophene Derivatives via Rhodium complexes: A Novel Approach to Condensed Benzo [2,1-b: 3, 4-b'] Dithiophenes", Helvetica Chimica Acta, 1997, pp. 111-120, vol. 80, No. 1.

Maximilian Zander, "Photoluminescence of Thiophee Benzologues, Zeitschrift fuer Naturforschung Teil A", Physik, Physikalische Chemie, Kosmophysik, 1985, pp. 497-502, vol. 40A, No. 5.

Chinese Patent Office Action issued Aug. 31, 2012 in counterpart application CN 200980104918.8.

* cited by examiner

FUSED RING COMPOUND, METHOD FOR PRODUCING THE SAME, POLYMER, ORGANIC THIN FILM CONTAINING THE COMPOUND AND/OR POLYMER, AND ORGANIC THIN FILM DEVICE AND ORGANIC THIN FILM TRANSISTOR EACH COMPRISING THE ORGANIC THIN FILM

CROSS REFERENCE TO RELATED APPLICATIONS

This application is a National Stage of International Application No. PCT/JP2009/052319 filed Feb. 12, 2009, claiming priority based on Japanese Patent Application No. 2008-032246 filed Feb. 13, 2008, the contents of all of which are incorporated herein by reference in their entirety.

TECHNICAL FIELD

The present invention relates to a fused ring compound, a method for producing the same, a polymer, an organic film containing the compound and/or the polymer, and an organic film device and an organic film transistor each comprising the organic film.

BACKGROUND ART

An organic semiconductor material is applied to various organic film devices such as an organic EL (electroluminescence) device, an organic transistor, an organic solar cell and a photosensor, and accordingly has been actively studied in recent years. In order to provide an excellent performance in these use applications, the organic semiconductor material is required to have high charge (electron or hole) transport properties. In order to provide high charge transport properties, it is important for the organic semiconductor material to use a molecule in which π-conjugation spreads, make the molecule adequately packed and enhance an interaction between molecules.

From such a viewpoint, a compound containing dithienothiophene (Patent Document 1), a compound in which a plurality of thiophene rings are planarly bonded together (Non-Patent Document 1) or the like are known as an organic semiconductor material providing high charge transport properties.

Patent Document 1: Japanese Patent Application Laid-Open Publication No. 2004-339516

Non-Patent Document 1: Z. Bao et al., "Appl. Phys. Lett.", 1996, 69, 4108.

DISCLOSURE OF THE INVENTION

Problem to be Solved by the Invention

However, though any of the above described compounds which are used as the organic semiconductor material has a high planarity of the molecule and excellent in charge transport properties as well, many of the compounds have been difficult to form an organic film or the like because these compounds do not have high solubility to a solvent. On the other hand, it is considered to enhance the solubility to the solvent by lowering the planarity of the molecule or the like, but in that case, the charge transport properties have tended to become insufficient.

Then, the present invention is designed with respect to such a circumstance, and is directed at providing a fused ring compound and a polymer which can show sufficient charge transport properties and also have excellent solubility into the solvent. The present invention is also directed at providing a method for producing the fused ring compound, an organic film using the fused ring compound and/or the polymer, and an organic film device and an organic film transistor each comprising the organic film.

In order to achieve the above described object, the fused ring compound of the present invention is represented by the following formula (1):

[Chemical Formula 1]

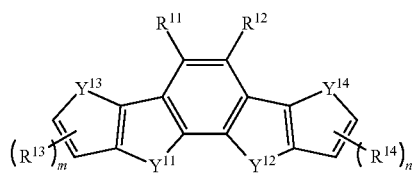

(1)

wherein $R^{11}$ and $R^{12}$ each independently represent a hydrogen atom, an alkyl group, an alkoxy group, an alkylthio group, an alkylamino group, an alkoxycarbonyl group having 3 or more carbon atoms in the alkyl moiety thereof, an aryl group that may have a substituent, a monovalent heterocyclic group that may have a substituent, or a cyano group, wherein at least one of $R^{11}$ and $R^{12}$ is not a hydrogen atom; $R^{13}$ and $R^{14}$ each independently represent a monovalent group and m and n each independently are an integer of 0 to 2, when there are a plurality of $R^{13}$s and a plurality of $R^{14}$s, the $R^{13}$s may be the same as or different from each other and the $R^{14}$s may be the same as or different from each other; $Y^{11}$ and $Y^{12}$ are each independently a divalent group represented by the following formula (2a), (2b), (2c), (2d), (2e), (2f), (2g) or (2h); and $Y^{13}$ and $Y^{14}$ are each independently a divalent group represented by the following formula (2a), (2b), (2c), (2d), (2e), (2f), (2g), (2h) or (2i):

[Chemical Formula 2]

(2a)

(2b)

(2c)

(2d)

(2e)

(2f)

(2g)

(2h)

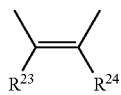
(2i)

wherein $R^{21}$, $R^{22}$, $R^{23}$ and $R^{24}$ each independently represent a hydrogen atom or a monovalent group, and $R^{23}$ and $R^{24}$ may be bonded together to form a ring.

Because the fused ring compound having the above described structure has a structure in which five aromatic ring structures are fused and π-conjugation spreads, the fused ring compound can show high charge transport properties when having formed the organic film or the like. In addition, such a fused ring compound has a structure in which a substituent is introduced into a central benzene ring structure. Therefore, the fused ring compound shows adequate solubility to the solvent or the like, and is easily processed to form the organic film or the like. In the present invention in particular, the fused ring compound has a structure in which fused rings having two rings are ring-fused in two portions with respect to the central benzene ring, and accordingly tends to provide higher charge transport properties than a structure in which the fused rings have one ring. Therefore, the fused ring compound of the present invention is useful as an organic semiconductor material for forming the organic film in the organic film device or the like.

In the fused ring compound of the above described present invention, $Y^{11}$ and $Y^{12}$ are preferably a divalent group that is represented by the above formula (2a), and $Y^{13}$ and $Y^{14}$ are preferably a divalent group represented by the above formula (2i). Thereby, the charge transport properties of the fused ring compound become more adequate. In addition, such a compound is comparatively easily synthesized, and another advantage thereof is the easy availability of the raw material.

Furthermore, it is preferable that $R^{11}$ and $R^{12}$ each independently represent an alkyl group having 1 to 10 carbon atoms or an aryl group having 6 to 20 carbon atoms, which may have a substituent. Thereby, the solubility of the fused ring compound to the solvent becomes more adequate.

In addition, the polymer of the present invention comprises a structure represented by the following formula (3), as a constitutional unit:

[Chemical Formula 3]

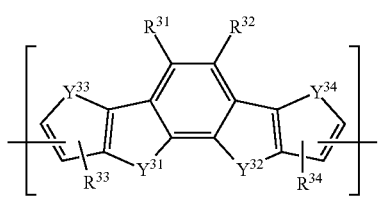
(3)

wherein $R^{31}$ and $R^{32}$ each independently represent a hydrogen atom, an alkyl group, an alkoxy group, an alkylthio group, an alkylamino group, an alkoxycarbonyl group having 3 or more carbon atoms in the alkyl moiety thereof, an aryl group that may have a substituent, a monovalent heterocyclic group that may have a substituent, or a cyano group, wherein at least one of $R^{31}$ and $R^{32}$ is not a hydrogen atom; $R^{33}$ and $R^{34}$ each independently represent a hydrogen atom or a monovalent group; $Y^{31}$ and $Y^{32}$ are each independently a divalent group represented by the following formula (4a), (4b), (4c), (4d), (4e), (4f), (4g) or (4h); and $Y^{33}$ and $Y^{34}$ are each independently a divalent group represented by the following formula (4a), (4b), (4c), (4d), (4e), (4f), (4g), (4h) or (4i):

[Chemical Formula 4]

(4a)

(4b)

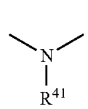
(4c)

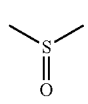
(4d)

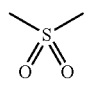
(4e)

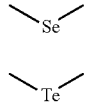
(4f)

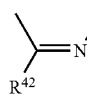
(4g)

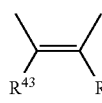
(4h)

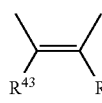
(4i)

wherein $R^{41}$, $R^{42}$, $R^{43}$ and $R^{44}$ each independently represent a hydrogen atom or a monovalent group; and $R^{43}$ and $R^{44}$ may be bonded together to form a ring.

Such a polymer has excellent electric-charge mobility and also becomes excellent in solubility to a solvent, because of containing the same fused ring structure as that of the above described fused ring compound of the present invention.

In addition, it is more preferable if the polymer of the present invention further has a structural unit represented by the following formula (5). Thereby, the electric-charge mobility of the polymer becomes further excellent.

[Chemical Formula 5]

(5)

wherein $Ar^5$ represents a divalent aromatic-hydrocarbon group which may have a substituent or a divalent heterocyclic group which may have a substituent.

Among them, it is preferable if the above described $Ar^5$ is a group represented by the following formula (6). Thereby, the electric-charge mobility of the polymer becomes particularly excellent.

[Chemical Formula 6]

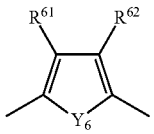
(6)

wherein $R^{61}$ and $R^{62}$ each independently represent a hydrogen atom or a monovalent group, and $R^{61}$ and $R^{62}$ may be bonded together to form a ring; $Y^6$ is a divalent group represented by the following formula (7a), (7b), (7c), (7d), (7e), (7f), (7g), (7h) or (7i):

[Chemical Formula 7]

(7a)

(7b)

(7c)

(7d)

(7e)

(7f)

(7g)

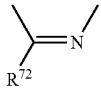
(7h)

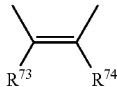
(7i)

wherein $R^{71}$, $R^{72}$, $R^{73}$ and $R^{74}$ each independently represent a hydrogen atom or a monovalent group, and $R^{73}$ and $R^{74}$ may be bonded together to form a ring.

In the polymer of the present invention, it is preferable if $Y^{31}$ and $Y^{32}$ are a divalent group represented by the above formula (4a), $Y^{33}$ and $Y^{34}$ are a divalent group represented by the above formula (4l), and $Y^6$ in the group represented by formula (6) is a divalent group represented by the above formula (7a). Thereby, the polymer results in acquiring further excellent electric-charge mobility and solubility.

A method for producing a fused ring compound of the present invention is a method of adequately forming the fused ring compound of the present invention, and includes making a compound represented by the following formula (8a) react with a compound represented by the following formula (8b) in the presence of a base and a metal complex catalyst to obtain a fused ring compound represented by the following formula (8c):

[Chemical Formula 8]

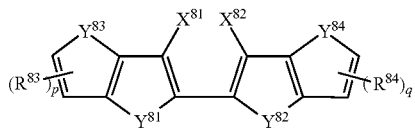
(8a)

(8b)

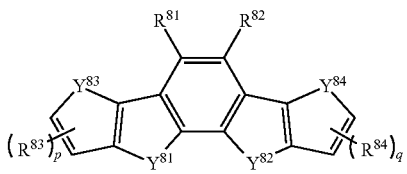
(8c)

wherein $X^{81}$ and $X^{82}$ each independently represent a hydrogen atom or a halogen atom, wherein at least one of $X^{81}$ and $X^{82}$ is a halogen atom; $R^{81}$ and $R^{82}$ each independently represent a hydrogen atom, an alkyl group, an alkoxy group, an alkylthio group, an alkylamino group, an alkoxycarbonyl group having 3 or more carbon atoms in the alkyl moiety thereof, an aryl group that may have a substituent, a monovalent heterocyclic group that may have a substituent, or a cyano group, wherein at least one of $R^{81}$ and $R^{82}$ is not a hydrogen atom; $R^{83}$ and $R^{84}$ each independently represent a monovalent group and p and q are each independently an integer of 0 to 2, when there are a plurality of $R^{83}$s and a plurality of $R^{84}$s, the $R^{83}$s may be the same as or different from each other and the $R^{84}$s may be the same as or different from each other; $Y^{81}$ and $Y^{82}$ each independently represent a divalent group represented by the following formula (9a), (9b), (9c), (9d), (9e), (9f), (9g) or (9h); and $Y^{83}$ and $Y^{84}$ each independently represent a divalent group represented by the following formula (9a), (9b), (9c), (9d), (9e), (9f), (9g), (9h) or (9i):

[Chemical Formula 9]

(9a)

(9b)

(9c)

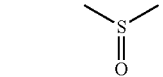
(9d)

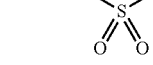
(9e)

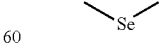
(9f)

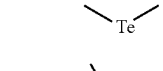
(9g)

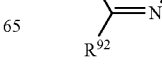
(9h)

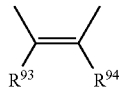
(9i)

wherein $R^{91}$, $R^{92}$, $R^{93}$ and $R^{94}$ each independently represent a hydrogen atom or a monovalent group; and $R^{93}$ and $R^{94}$ may be bonded together to form a ring.

According to such a method of producing the fused ring compound, a fused ring compound can be obtained only by reacting the compound of the above formula (8a) with the compound of the above formula (8b), and accordingly a fused ring compound of the present invention can be simply obtained.

In such a production method, it is preferable if $Y^{81}$ and $Y^{82}$ are a divalent group represented by the above formula (9a), and $Y^{83}$ and $Y^{84}$ are a divalent group represented by the above formula (9i). Thereby, the fused ring compound is obtained which is further excellent in charge transport properties. Such a compound is comparatively easily synthesized, and accordingly the fused ring compound can be easily produced by using such a compound.

In addition, at least one of $X^{81}$ and $X^{82}$ is a halogen atom, but it is more preferable if both of them are a halogen atom. It is further preferable if at least one of $X^{81}$ and $X^{82}$ are an iodine atom in particular, and it is particularly preferable that both of them are the iodine atom. Thereby, the compound represented by the above formula (8a) becomes to easily react with the compound represented by the above formula (8b), and the compound represented by the above formula (8c) can be produced more efficiently.

The present invention provides also an organic film containing the fused ring compound and/or the polymer of the present invention. Such an organic film has excellent charge transport properties because of containing the above described fused ring compound and/or the polymer of the present invention, and is suitable for an organic film device or the like.

The present invention provides also the organic film device having the organic film of the present invention. An organic film transistor is preferable as such an organic film device. These organic film devices results in being capable of showing excellent characteristics because of having an organic film of the present invention, of which the charge transport properties are high.

Effect of the Invention

The present invention can provide a fused ring compound and a polymer which can show sufficient charge transport properties and also have excellent solubility to a solvent. The present invention can provide also a suitable method for producing the above described fused ring compound. The present invention can further provide an organic film which is obtained by using the above described fused ring compound and has excellent charge transport properties, and an organic film device and an organic film transistor each comprising the organic film.

DESCRIPTION OF SYMBOLS

Figure 1:
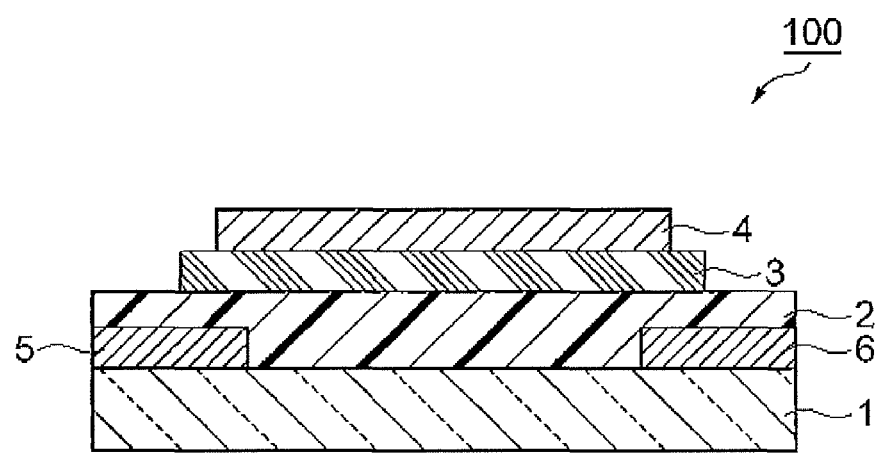
FIG. 1 is a schematic sectional view of an organic film transistor according to a first embodiment.

1 . . . substrate, 2 . . . active layer, 2a . . . active layer, 3 . . . insulation layer, 4 . . . gate electrode, 5 . . . source electrode, 6 . . . drain electrode, 7a . . . first electrode, 7b . . . second electrode, 8 . . . electric-charge-generating layer, 100 . . . organic film transistor according to first embodiment, 110 . . . organic film transistor according to second embodiment, 120 . . . organic film transistor according to third embodiment, 130 . . . organic film transistor according to fourth embodiment, 140 . . . organic film transistor according to fifth embodiment, 150 . . . organic film transistor according to sixth embodiment, 160 . . . organic film transistor according to seventh embodiment, 200 . . . solar cell according to embodiment, 300 . . . photosensor according to first embodiment, 310 . . . photosensor according to second embodiment, and 320 . . . photosensor according to third embodiment.

BEST MODES FOR CARRYING OUT THE INVENTION

Preferred embodiments according to the present invention will be described in detail below with reference to the drawings as needed. In the description for the drawings, the same reference numeral will be put on the same element and the description on the same element will be omitted.

[Fused Ring Compound]

Firstly, the fused ring compound according to preferred embodiments will be described below. The fused ring compound of the present embodiment is a compound represented by the above formula (1). In the compound represented by the above formula (1), the group represented by $R^{11}$ or $R^{12}$ is a hydrogen atom, an alkyl group, an alkoxy group, an alkylthio group, an alkylamino group, an alkoxycarbonyl group having 3 or more carbon atoms in the alkyl moiety thereof, an aryl group which may have a substituent, a monovalent heterocyclic group which may have a substituent, or a cyano group. At least one of $R^{11}$ and $R^{12}$ is not a hydrogen atom, and it is preferable that either of them is not a hydrogen atom. In the above description, the alkyl group includes straight-chain, branched and cyclic alkyl groups. In the above described functional groups, one part or all of hydrogen atoms in the functional group may be substituted with halogen atoms (fluorine atoms in particular).

Here, it is preferable that the alkyl group has 1 to 20 carbon atoms (which is abbreviated as "C1 to 20", hereinafter the same). Such an alkyl group includes, for instance, a methyl group, an ethyl group, an n-propyl group, an iso-propyl group, an n-butyl group, an iso-butyl group, a sec-butyl group, a tert-butyl group, a pentyl group, a hexyl group, a heptyl group, an octyl group, a nonyl group, a decyl group, a lauryl group, a cyclopropyl group, a cyclopentyl group, a cyclohexyl group, a cycloheptyl group, a cyclooctyl group, a cyclononyl group and a cyclododecyl group. Among them, the alkyl group of C1 to 16 is preferable, and the alkyl group of C6 to C12 is more preferable, from the viewpoint of more adequately enhancing the solubility to the solvent. For instance, a hexyl group, a heptyl group, an octyl group, a decyl group or a cyclohexyl group is preferable.

As for the alkoxy group, the alkylthio group, the alkylamino group or the alkoxycarbonyl group, the alkyl group possessed by these groups is preferably an alkyl group of C1 to 20. However, the number of carbon atoms in the alkyl group possessed by the alkoxycarbonyl group is 3 or more. Examples of the alkyl group of C1 to 20 can include similar groups to those described in the above.

As for the aryl group which may have a substituent, an aryl group of C6 to 60 is preferable. The aryl group includes, for instance, a phenyl group, a phenyl group having an alkoxy group of C1 to 12, a phenyl group having an alkyl group of C1 to 12, a 1-naphthyl group and a 2-naphthyl group. Among them, an aryl group of C6 to 20 is preferable, and the phenyl group having an alkoxy group of C1 to 12 or the phenyl group having an alkyl group of C1 to 12 is further preferable.

As for the monovalent heterocyclic group which may have a substituent, a monovalent heterocyclic group of C3 to 60 is preferable. The monovalent heterocyclic group includes, for instance, a thienyl group, a thienyl group having an alkyl group of C1 to 12, a pyrrolyl group, a furyl group, a pyridyl group and a pyridyl group having an alkyl group of C1 to 12. Among them, a heterocyclic group of C3 to 20 is preferable, and the thienyl group, the thienyl group having the alkyl group of C1 to 12, the pyridyl group or the pyridyl group having the alkyl group of C1 to 12 is more preferable. In the above description, the heterocyclic group shall mean a group in which at least one atom constituting a ring in an organic group having a cyclic structure is a hetero atom.

In the fused ring compound, among the above described compounds, $R^{11}$ and $R^{12}$ are preferably each independently an alkyl group having 1 to 20 carbon atoms or an aryl group which may have a substituent having 6 to 60 carbon atoms, are more preferably an alkyl group having 1 to 14 carbon atoms or an aryl group which may have a substituent having 6 to 20 carbon atoms, and are particularly preferably the aryl group having 1 to 14 carbon atoms.

In addition, $R^{13}$ and $R^{14}$ are each independently a monovalent group, and m and n are an integer of 0 to 2. However, when m or n is 2, a plurality of $R^{13}$ or $R^{14}$ may be each the same group or different groups. $R^{13}$ and $R^{14}$ include an alkyl group, an alkoxy group, a fluoroalkyl group, a fluoroalkoxy group, an aryl group, an arylamino group or a monovalent heterocyclic group. Among them, the alkyl group, the alkoxy group, the fluoroalkyl group, the fluoroalkoxy group, the aryl group or the arylamino group is preferable, and the alkyl group or the aryl group is further preferable. For information, it is preferable that $R^{13}$ and $R^{14}$ are appropriately changed according to the carrier which the organic film containing the fused ring compound should transport. For instance, when the hole transport properties of the organic film are enhanced, an electron-donating group such as an arylamino group is preferable, and from the view point of enhancing electron transport properties, an electron-attracting group such as a fluoroalkyl group and a fluoroalkoxy group is preferable.

In addition, the monovalent group represented by $R^{13}$ and $R^{14}$ includes a polymerizable functional group as well. When at least one of $R^{13}$ and $R^{14}$ is the polymerizable functional group in particular, the fused ring compound represented by the formula (1) becomes preferable for a raw material of a polymer which will be described later. Incidentally, when the organic film is formed of only the fused ring compound, it is preferable that $R^{13}$ and $R^{14}$ are the above described groups except the polymerizable functional group.

Here, the polymerizable functional group means a group which can cause a polymerization reaction between itself and another polymerizable functional group. The polymerizable functional group means the group which can form a bond with another polymerizable functional group by reacting with the polymerizable functional group by being supplied, for instance, to a Wittig reaction, a Heck reaction, a Horner-Wadsworth-Emmons reaction, a Knoevenagel reaction, a Suzuki coupling reaction, a Grinard reaction, a Stille reaction, a polymerization reaction with the use of an Ni (O) catalyst or the like.

Examples of such a polymerizable functional group can include a halogen atom, an alkyl sulfonate group, an aryl sulfonate group, an aryl alkyl sulfonate group, an alkyl stannyl group, an aryl stannyl group, an aryl alkyl stannyl group, a boric ester residue, a sulfonium methyl group, a phosphonium methyl group, a methyl phosphonate group, a monohalogenomethyl group, a boric acid residue (—B(OH)$_2$), a formyl group and a vinyl group. Among them, the halogen atom, the alkyl stannyl group or the boric ester residue is preferable. For information, R in these examples is an alkyl group or an aryl group, and two Rs may be bonded together to form a ring. The boric acid residue means a group in which hydroxy groups substitute for bonds of boron. Furthermore, the boric ester residue is a monovalent group having a structure in which one bond of boron atoms in a boric ester is substituted with a bond for substitution, and includes such a group as is expressed by the following formulae (100a) to (100d), for instance.

[Chemical Formula 10]

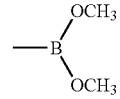

(100a)

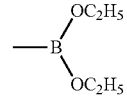

(100b)

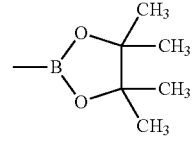

(100c)

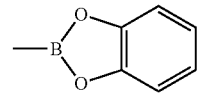

(100d)

In the above formula (1), $Y^{11}$ and $Y^{12}$ each independently represent a divalent group represented by the above formula (2a), (2b), (2c), (2d), (2e), (2f), (2g) or (2h) (which will be referred to as "(2a) to (2h)", hereinafter). $R^{21}$ and $R^{22}$ in these divalent groups each independently represent a hydrogen atom or a monovalent group. This monovalent group includes a halogen atom in addition to similar groups to the above described $R^{11}$ and $R^{12}$. For information, the group represented by the above formula (2h) has an asymmetrical structure, but the direction in which the bonding chain is bonded is not limited in particular.

Among them, a divalent group represented by the above formula (2a), (2b), (2c) or (2h) is preferable for $Y^{11}$ and $Y^{12}$, and a divalent group represented by the above formula (2a), (2b) or (2c) is more preferable. In addition, when $Y^{11}$ and $Y^{12}$ are the divalent group represented by the above formulae (2a), (2b) or (2c), the ring structure containing these groups (two five-membered rings which are fused to a benzene ring having $R^{11}$ and $R^{12}$ as a substituent) becomes a thiophene ring, a furan ring or a pyrrole ring, respectively. It is particularly preferable if $Y^{11}$ and $Y^{12}$ are the divalent groups that are expressed by the above formula (2a) (in other words, having the ring structure of a thiophene ring), because adequate charge transport properties can be obtained.

In the above formula (1), $Y^{13}$ and $Y^{14}$ each independently represent a divalent group represented by the above formula (2a), (2b), (2c), (2d), (2e), (2f), (2g), (2h) or (2i) (which is referred to as "(2a) to (2i)", hereinafter). $R^{21}$, $R^{22}$, $R^{23}$ and $R^{24}$ in these divalent groups each independently represent a hydrogen atom or a monovalent group, and $R^{23}$ and $R^{24}$ may be bonded together to form a ring. This monovalent group includes a halogen atom in addition to similar groups to the above described $R^{11}$ and $R^{12}$. In addition, similarly to the above description, in the group represented by the above formula (2h), the direction in which the bonding chain is bonded is not limited in particular.

Among them, a divalent group represented by the above formula (2a), (2b), (2c), (2h) or (2i) is preferable for $Y^{13}$ and $Y^{14}$, and a divalent group represented by the above formula (2a), (2b), (2c) or (2i) is more preferable. In addition, when $Y^{13}$ and $Y^{14}$ are the divalent group represented by the above formula (2a), (2b), (2c) or (2i), the ring structures containing these groups (two five-membered rings or six membered-rings which are fused to the ring structure containing $Y^{11}$ and $Y^{12}$) become a thiophene ring, a furan ring, a pyrrole ring or a benzene ring, respectively. It is more preferable that $Y^{13}$ and $Y^{14}$ are particularly the divalent group represented by the above formula (2a)(in other words, having a ring structure of a thiophene ring) or the divalent group represented by the above formula (2i) (in other words, having the ring structure of a benzene ring), and it is further preferable if $Y^{13}$ and $Y^{14}$ are the divalent group represented by the above formula (2i) because particularly adequate charge transport properties are obtained.

Preferred examples of the fused ring compound as described above include a compound represented by the following formula (1a) or (1b). For information, $R^{11}$, $R^{12}$, $R^{13}$, $R^{14}$, n and m in the following formulae are synonymous with the above description.

[Chemical Formula 11]

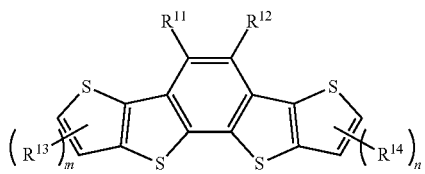

(1a)

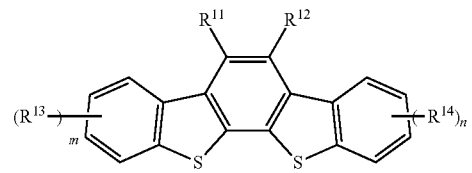

(1b)

[Polymer]

Next, a polymer according to preferred embodiments will be described below. The polymer of the present embodiment has a structural unit represented by the above formula (3). In the polymer, this structural unit is contained as at least one of the structural units constituting the main chain of the polymer. In the polymer of the present embodiment, it is preferable if the amount of the structural unit represented by the above formula (3) contained in all structural units constituting the main chain of the polymer is 30 mol % or more, and it is more preferable if the amount of the structural unit is 50 mol % or more.

In the structure represented by the formula (3), $R^{31}$, $R^{32}$, $R^{33}$, $R^{34}$, $Y^{31}$, $Y^{32}$, $Y^{33}$ and $Y^{34}$ are preferably similar groups to the above described $R^{11}$, $R^{12}$, $R^{13}$, $R^{14}$, $Y^{11}$, $Y^{12}$, $Y^{13}$ and $Y^{14}$, respectively. However, $R^{33}$ and $R^{34}$ are preferably groups except the above described polymerizable functional group. In the above description, the polymer in the present embodiment means a compound having two or more structural units formed from one monomer, and shall contain both of compounds which are usually classified into an oligomer and a polymer.

The polymer in the present embodiment may be a polymer which is constituted by only the structural unit of the above formula (3), and may also further contain another monomer unit. At this time, the plurality of the structural units of the above formula (3) results in being contained in the polymer, but the plurality of the structural units of the above formula (3) may be each the same structure or different structures. However, from the viewpoint of easily obtaining the polymer, it is preferable if the plurality of the structural units of the formula (3) are each the same structure.

It is also preferable that the polymer further has the structural unit of the above formula (5) in addition to the monomer unit of the above formula (3) as a structural unit constituting the main chain. Thus, the polymer has the structural unit of the formula (5), thereby further enhances charge transport properties of the polymer, and also enhances solubility to a solvent, mechanical strength, heat resistance and the like as well.

A group represented by $Ar^5$ in the structural unit of the formula (5) is a divalent aromatic hydrocarbon group which may have a substituent or a divalent heterocyclic group which may have a substituent. Such a divalent aromatic hydrocarbon group or a divalent heterocyclic group is a group having a structure in which substitution sites in two portions are supplied for bonding in the polymer in the aromatic hydrocarbon group or the heterocyclic group, in other words, is a group containing an atom group which is left after two hydrogen atoms have been removed from the aromatic hydrocarbon group or the heterocyclic group.

A divalent aromatic hydrocarbon group formed of an aromatic ring (monocycle or fused ring) preferably of C6 to 60 and more preferably of C6 to 20 is preferable for the divalent aromatic hydrocarbon group constituting the group represented by $Ar^5$. Examples of the fused ring can include a naphthalene ring, an anthracene ring, a tetracene ring, a pentacene ring, a pyrene ring, a perylene ring and a fluorene ring. Among them, a benzene ring, the pentacene ring, the pyrene ring or the fluorene ring is preferable for the aromatic ring constituting this aromatic hydrocarbon group. In addition, the aromatic hydrocarbon group may also further have a substituent as was described above. Examples of such a substituent can include a halogen atom, a saturated or unsaturated hydrocarbon group, an aryl group, an alkoxy group, an aryloxy group, a monovalent heterocyclic group, an amino group, a nitro group and a cyano group.

In addition, a divalent group formed of a heterocycle preferably of C3 to 60 and more preferably of C3 to 20 is preferable for the divalent heterocyclic group. The divalent heterocyclic group includes, for instance, a group formed of the atom group which is left after two hydrogen atoms have been removed from thiophene, a compound in which 2 to 6 pieces of thiophene rings are ring-fused such as thienothiophene, dithienothiophene or the like, thiazole, pyrrole, pyridine, pyrimidine, pyrazine, triazine or the like; and a group formed of the atom group is preferable which is left after two hydrogen atoms have been removed from thiophene, the compound in which 2 to 6 pieces of thiophene rings are ring-fused such as thiophene, thieno thiophene, dithienothiophene or the like. Such a divalent heterocyclic group may also have a substituent, and such a substituent includes similar substituents to those in the above described aromatic hydrocarbon group.

In the structural unit of the formula (5), a group represented by the above formula (6) is preferable for the group represented by $Ar^5$. A similar group to $Y^{11}$ or $Y^{12}$ in the above formula (1) is preferable for the group represented by $Y^6$ in the formula (6). It is particularly preferable if $Y^6$ in the group represented by the formula (6) is a group represented by the above formula (7a).

When the polymer includes both of the structural unit represented by the above formula (3) and the structural unit represented by the above formula (5), a suitable ratio of these structural units in the polymer is such a ratio that the structural unit represented by the formula (5) is preferably 10 to 1,000 mol with respect to 100 mol of the monomer unit of the formula (3), more preferably is 25 to 400 mol, and further preferably is 50 to 200 mol.

A polymer containing the structural unit represented by the above formula (3) and the structural unit represented by the above formula (5) in combination is preferable for the polymer in the present embodiment. In the polymer, these structural units may be copolymerized at random, or may be copolymerized in a block. Examples of such a polymer can include a polymer having a structure represented by the following formula (10a) or (10b).

[Chemical Formula 12]

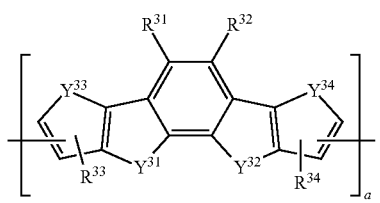

(10a)

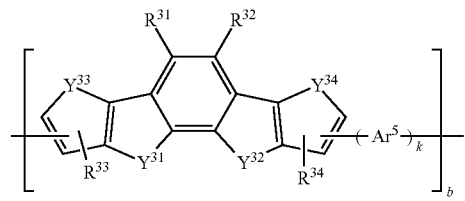

In the formula, any of $R^{31}$ to $R^{34}$, $Y^{31}$ to $Y^{34}$, and $Ar^5$ is synonymous with the above description. Suffix k is an integer of 1 to 10. When the k is 2 or more and a plurality of $Ar^5$ exist, these may be the same or different. In addition, a is preferably an integer of 2 to 500, and more preferably is an integer of 3 to 20. Furthermore, b is preferably an integer of 1 to 500, and more preferably is an integer of 2 to 20. In these polymers, a polymer is particularly preferable in which both of $Y^{31}$ and $Y^{32}$ are a sulfide group, both of $Y^{33}$ and $Y^{34}$ are a vinylene group, $R^{31}$ and $R^{32}$ are each independently an alkyl group or an aryl group (preferably the alkyl group), and $R^{33}$ and $R^{34}$ are a hydrogen atom.

A terminal group of such a polymer is not limited in particular, but includes an electron-attracting group or an electron-donating group such as a hydrogen atom, an alkyl group, an alkoxy group, a fluoroalkyl group, a fluoroalkoxy group, an aryl group and a heterocyclic group. From the viewpoint of enhancing the electron transport properties of the polymer, it is preferable that the terminal group is the electron-attracting group such as the fluoroalkyl group and the fluoroalkoxy group. The terminal group may have also a structure which can conjugate with a conjugate structure of the main chain, and such a terminal group includes, for instance, an aryl group having an unsaturated bond in a site to be bonded with the main chain or a monovalent heterocyclic group.

When the fused ring compound which has a polymerizable functional group for a group represented by $R^{13}$ and $R^{14}$ in the above formula (1) is used as a raw monomer in the production of the polymer, the polymerizable functional group results in remaining in the terminal after polymerization. However, when the organic film has been formed, the terminal formed of this polymerizable functional group may decrease the durability or the like. Accordingly, in the polymer, it is preferable to protect the polymerizable functional group with a stable group.

More specifically, compounds that are expressed by the following formulae (11a) to (11p) are preferable for the polymer of the present embodiment.

[Chemical Formula 13]
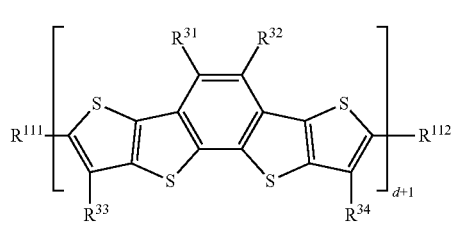 (11a)
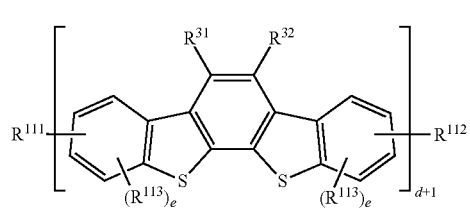 (11b)
[Chemical Formula 14]
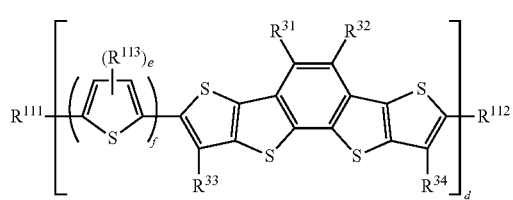 (11c)
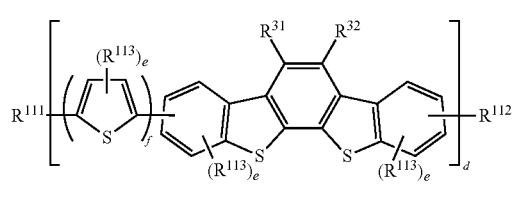 (11d)
[Chemical Formula 15]
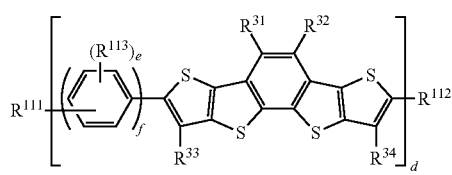 (11e)
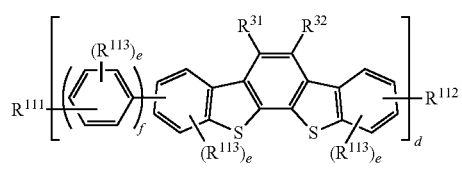 (11f)
[Chemical Formula 16]
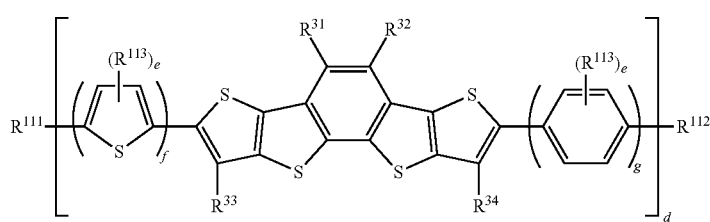 (11g)
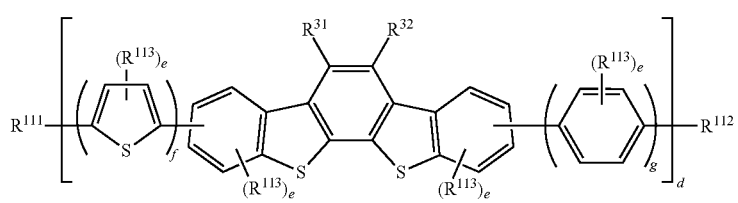 (11h)
[Chemical Formula 17]
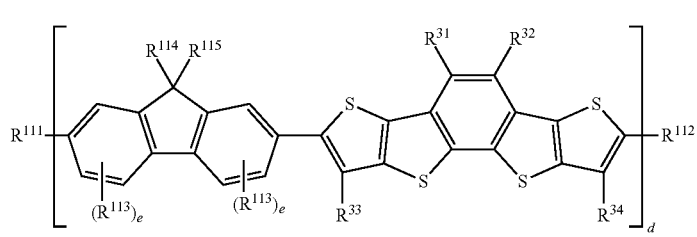 (11i)

-continued
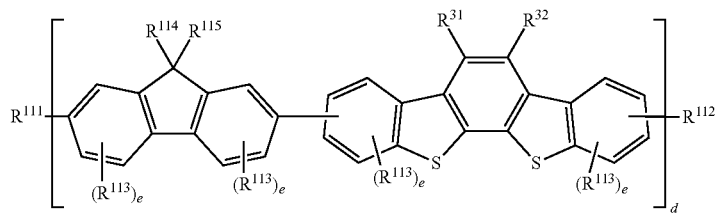
(11j)
[Chemical Formula 18]
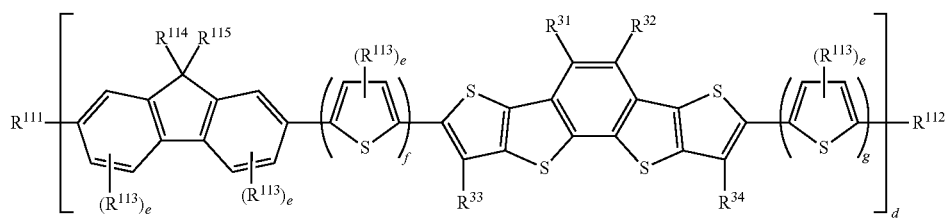
(11k)
(11l)
[Chemical Formula 19]
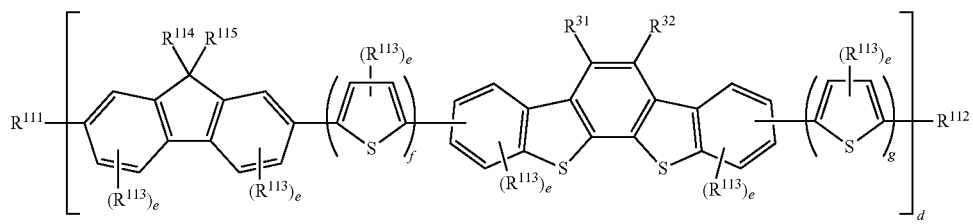
(11m)
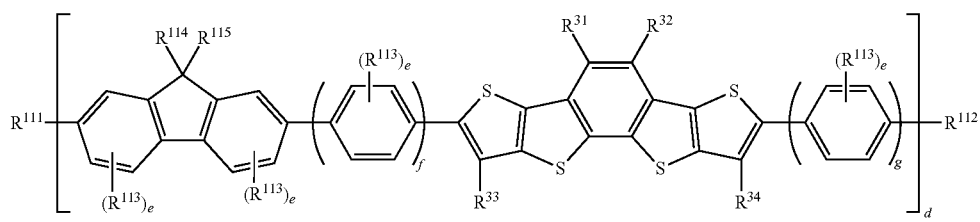
(11n)
[Chemical Formula 20]
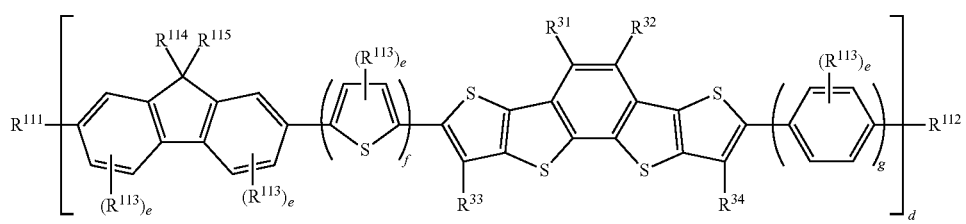
(11o)

-continued

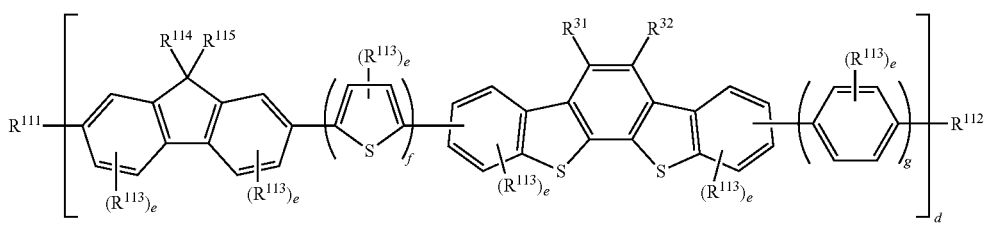

(11p)

In the above formulae (11a) to (11p), $R^{31}$ to $R^{34}$ are synonymous with the above description. $R^{111}$ and $R^{112}$ each independently represent the above described terminal group. $R^{113}$ represents a monovalent group. $R^{114}$ and $R^{115}$ each independently represent a hydrogen atom or a monovalent group. These monovalent groups include similar groups to $R^{13}$, $R^{14}$ and the like in the above formula (1). Among them, an alkyl group or an alkoxy group is preferable, and the alkyl group is more preferable. In the formula, d represents an integer of 1 to 500, e represents an integer from 0 to the number of substitutable sites in a ring to which $R^{113}$ is bonded. Suffix f represents an integer of 1 to 3, and g represents an integer of 0 to 3. However, when e, f or g is 2 or more, a plurality of groups or structural units in parentheses to which these are suffixed result in existing, but they may be each the same or different.

Here, it is preferable that the value of d is appropriately selected according to a method of forming the organic film with the use of the polymer. When the organic film is formed with a vapor deposition method such as a vacuum vapor deposition method, for instance, an oligomer having d of preferably 1 to 10, more preferably 2 to 10 and further preferably 2 to 5, for the polymer is preferable. In addition, when the organic film is formed with a method of applying a solution in which the polymer has been dissolved in an organic solvent, the polymer has d of preferably 3 to 500, more preferably 6 to 300 and further preferably 20 to 200. Furthermore, when the film is formed by application, it is preferable if the number average molecular weight of the polymer is $1 \times 10^3$ to $1 \times 10^8$ in terms of polystyrene, and it is further preferable if the number average molecular weight is $1 \times 10^4$ to $1 \times 10^6$, from the viewpoint of enhancing the uniformity of the film.

In addition, the polymer has a structure in which the structural units in the parenthesis in each of the above formulae repeat several times, but the plurality of the structural units in the polymer may have each the same or different structure. In other words, the functional group of $R^{113}$ to $R^{115}$ and the like in the structural unit may be the same or different in repeating units. However, it is preferable that all structural units have the same structure, from the viewpoint of easily producing the polymer.

[Method for Producing Fused Ring Compound]

Next, a preferable method for producing the fused ring compound having the above described structure will be described below. The fused ring compound can be obtained by making the compound represented by the above formula (8a) react with the compound represented by the above formula (8b) in the presence of a base and a metal complex catalyst. In such a production method, a reaction occurs between the group represented by $X^{81}$ and $X^{82}$ in the compound represented by the formula (8a) and a triple bond in the compound represented by the formula (8b), thereby two fused rings in the compound represented by the formula (8a) are cross-linked, and a six-membered-ring structure is formed between these. Incidentally, it is preferable to conduct this reaction under an atmosphere of an inert gas such as nitrogen and argon.

In the compound of the above formula (8a), similar groups to the groups that are expressed by $R^{13}$, $R^{14}$, $Y^{11}$, $Y^{12}$, $Y^{13}$ and $Y^{14}$ in the above formula (1) can be applied to $R^{83}$, $R^{84}$, $Y^{81}$, $Y^{82}$, $Y^{83}$ and $Y^{84}$, respectively. In addition, $X^{81}$ and $X^{82}$ each independently represent a hydrogen atom or a halogen atom, and it is preferable if both of them are a halogen atom. More specifically, it is preferable if at least one of $X^{81}$ and $X^{82}$ is an iodine atom, and it is more preferable if both of them are an iodine atom. If $X^{81}$ and $X^{82}$ are an iodine atom, the above described reaction tends to extremely easily occur. In addition, similar compounds to $R^{11}$ and $R^{12}$ in the above formula (1) can be applied to $R^{81}$ and $R^{82}$ in the compound of the formula (8b).

The metal complex catalyst in the above described reaction includes, for instance, a palladium complex, a nickel complex, a platinum complex, a ruthenium complex, a rhodium complex or an iridium complex. Among them, the palladium complex or the nickel complex is preferable, and the palladium complex is more preferable. The palladium complex is not limited in particular, but a palladium complex which can promote the coupling reaction of the aromatic halide is preferable. This palladium complex includes, for instance, a divalent palladium complex and a palladium complex compound having an electron-donating ligand.

Examples of the divalent palladium complex can include palladium acetate, palladium chloride, sodium palladate and potassium palladate, and the palladium acetate is preferable. The palladium complex compound having the electron-donating ligand includes tetrakis(triphenyl phosphine)palladium, dichloro bis(triphenyl phosphine)palladium and tris(dibenzylidene acetone)dipalladium, and the tetrakis(triphenyl phosphine)palladium is preferable.

The above described metal complex catalysts may be applied solely, or a plurality of the types may be applied in combination. The metal complex catalyst in an amount of preferably 0.01 to 50 mol %, more preferably 1.0 to 20 mol % and further preferably 3 to 15 mol % is used with respect to the compound represented by the formula (8a), which is a raw material.

Both of an inorganic base and an organic base can be applied to the base which is used for the above described reaction, and the organic base is more preferable. The inorganic base includes a hydroxide, a carbonate, an ammonium salt and an acetate of an alkaline metal or an alkaline earth metal. The organic base includes pyridine in addition to amines such as a trialkylamine, a dialkyl arylamine, an alkyl diaryl amine and a triaryl amine, which contain an alkyl group of C1 to 20.

The organic base includes, specifically, trimethyl amine, triethylamine, diisopropyl ethyl amine, tri-n-propylamine, tributyl amine, dicyclohexyl methylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine and 3,5,6-collidine.

Amines are particularly preferable as the organic base. By using the amines as the base, it becomes possible to suppress the production of a by-product in the reaction and to obtain a target fused ring compound at a high yield. Among amines, an alkylamine is preferable, and the trialkylamine is particularly preferable. An alkylamine having a structure in which a carbon atom adjacent to a nitrogen atom has one or more hydrogen atoms, in other words, having a structure represented by N—CHx (X=integer of 1 to 3) is preferable for such an alkylamine, and an alkylamine having a structure in which a carbon atom adjacent to a nitrogen atom has two or more hydrogen atoms, in other words, having a structure represented by N—CHx (X=integer of 2 to 3) is more preferable.

The above described reaction can be conducted also in a solvent. A solvent inert to the reaction due to the metal complex catalyst is preferable for the solvent used for the reaction. The solvent includes, for instance, toluene, dimethylformamide (DMF), N-methyl-2-pyrrolidone (NMP), tetrahydrofuran (THF), dioxane, isopropyl alcohol, acetonitrile and pinacolone. Among them, the toluene, the NMP or the dioxane is preferable. The quantity of the solvent to be used is not limited in particular, but can be preferably set at a quantity of 1 to 100 times with respect to the weight of the compound represented by the formula (8a), which is the raw material, and can be more preferably set at a quantity of 2 to 30 times, for instance.

The reaction time is not limited in particular, but the reaction can be finished when either one of the compounds that are expressed by the formula (8a) or the compound represented by the formula (8b) has been used up. The time to be spent by the end of the reaction from the start is approximately 0.5 to 200 hours. In addition, the reaction temperature can be appropriately set in a range of −50 to 300° C., and can be preferably set approximately in a range of 50 to 150° C.

In order to obtain an organic film of high purity, it is preferable to refine the obtained fused ring compound by distillation, sublimation, recrystallization or the like, after the above described reaction.

The fused ring compound is adequately obtained by the above described production method. In such a production method, the reaction represented by the following reaction formula occurs, though the reaction is not limited in particular, and the fused ring compound represented by the following formula (8c) is obtained.

[Chemical Formula 21]

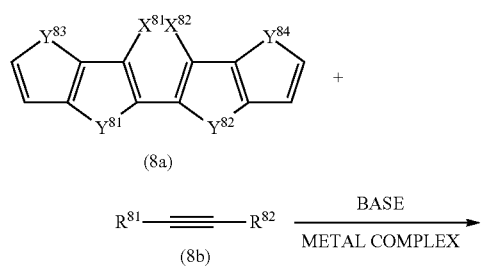

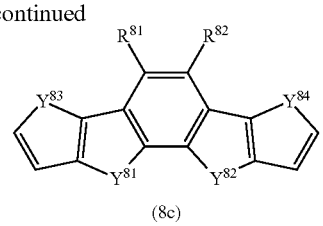

(8c)

[Method for Producing the Polymer]

Next, a preferable method for producing the polymer having the above described structure will be described below. In the following description, a method for producing the polymer having both of the monomer unit represented by the above formula (3) and the monomer unit represented by the above formula (5) will be described.

The polymer can be obtained by making the monomer represented by the following formula (13a) react with the monomer represented by the following formula (13b) to convert them to a high molecule.

[Chemical Formula 22]

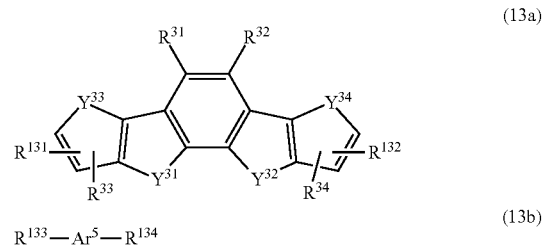

In the formulae, any of $R^{31}$ to $R^{34}$, $Y^{31}$, $Y^{32}$, $Y^{33}$ and $Y^{34}$ are synonymous with the above description. In addition, $R^{131}$ to $R^{134}$ are each independently a polymerizable functional group. However, $R^{33}$ and $R^{34}$ are preferably a group except for the polymerizable functional group. The polymerizable functional group includes similar groups to the groups illustrated as the polymerizable functional groups of $R^{13}$ and $R^{14}$ in the above formula (1).

In order to obtain the polymer, the reaction of forming a bond between the compound represented by the above formula (13a) and the compound represented by the above formula (13b), between compounds that are expressed by the formula (13a) or between compounds that are expressed by the formula (13b) is repeated. The above described reaction of forming the bond between the compounds includes a Wittig reaction, a Heck reaction, a Horner-Wadsworth-Emmons reaction, a Knoevenagel reaction, a Suzuki coupling reaction, a Grinard reaction, a Stille reaction and a polymerization reaction with the use of an Ni (O) catalyst. In addition to the above reactions, a reaction caused by the decomposition of an intermediate compound having an adequate leaving group also can be applied. The reaction includes, for instance, a method of synthesizing poly(p-phenylene vinylene) from an intermediate compound having a sulfonium group. It is preferable to appropriately select the above described polymerizable functional group of $R^{131}$ to $R^{134}$ according to the target reaction. In addition, the polymer may be formed by another method than the reaction caused by the polymerizable functional group. For instance, the method includes also a method of repeatedly bonding fused ring compounds of which m and n are 0 in the above formula (1) together by an oxidative polymerization reaction with the use of $FeCl_3$, a polymerization reaction due to the electrochemical oxidation, or the like.

Among the above described reactions, the Suzuki coupling reaction, the Grinard reaction, the Stille reaction and the polymerization reaction with the use of an Ni (O) catalyst are preferable for the reaction for obtaining the polymer, because the structure is easily controlled, the raw material is comparatively easily prepared, and besides, the reaction is simply operated. The oxidative polymerization reaction with the use of $FeCl_3$ is also preferable because the raw material is comparatively easily prepared and besides, the reaction is simply operated.

A combination of the polymerizable functional group suitable for these reactions includes, specifically, a combination of a boric acid residue or a boric ester residue and a halogen atom in the case of the Suzuki coupling reaction, and a combination of a halo-magnesium carbanion and the halogen atom in the case of the Grinard reaction. In addition, the combination includes a combination of the alkyl stannyl group and the halogen atom in the case of the Stille reaction, and a mutual combination of halogen atoms in the case of the polymerization reaction with the use of an Ni (O) catalyst.

It is preferable that the reaction for obtaining the polymer is conducted in an inert atmosphere so as to suppress a side reaction. From the viewpoint of obtaining an organic film of high purity from the polymer, it is desirable to refine the monomer of the raw material beforehand with various methods such as distillation, sublimation, recrystallization and the like. Furthermore, after the reaction, the product is extracted by an organic solvent, the solvent is distilled off, and then, the polymer of the target product is isolated from the extract, but it is preferable that this polymer is further refined by means of chromatography, recrystallization and the like.

In addition, each of the above described reactions can be caused in a solution in which the raw monomer has been dissolved in a solvent. In this case, it is preferable to dissolve the raw material in the solvent by adding a base, a catalyst or the like thereto as needed, and then to conduct the reaction at a temperature of the boiling point of the solvent or lower.

A preferred solvent varies depending on a reaction to be caused, but examples of the solvent can include: a saturated hydrocarbon such as pentane, hexane, heptane, octane and cyclohexane; an aromatic hydrocarbon such as benzene, toluene, ethylbenzene and xylene; a halogenated saturated hydrocarbon such as carbon tetrachloride, chloroform, dichloromethane, chlorobutane, bromobutane, chloropentane, bromopentane, chlorohexane, bromohexane, chlorocyclohexane and bromocyclohexane; a halogenated aromatic hydrocarbon such as chlorobenzene, dichlorobenzene and trichlorobenzene; alcohols such as methanol, ethanol, propanol, isopropyl alcohol, butanol and t-butyl alcohol; carboxylic acids such as formic acid, acetic acid and propionic acid; ethers such as dimethylether, diethyl ether, methyl-t-butyl ether, tetrahydrofuran, tetrahydropyran and dioxane; and an inorganic acid such as hydrochloric acid, bromic acid, hydrofluoric acid, sulfuric acid and nitric acid. These may be used in combination of a plurality of types, as needed. In addition, it is preferable to use a solvent which has been subjected to a sufficient deoxidation treatment, from the viewpoint of suppressing a side reaction.

[Organic Film]

Next, the organic film according to a preferred embodiment will be described below. The organic film has a structure which contains the fused ring compound and the polymer according to the above described embodiment and has a membranal shape. The organic film may contain only either one of the fused ring compound or the polymer, and may also contain both of them. In addition, in the organic film, two or more types of the fused ring compounds or the polymers may be contained in combination, respectively.

Furthermore, the organic film may include only the fused ring compound or the polymer, or may further include other components. The preferable thickness of such an organic film varies depending on a device to which the organic film is applied, but usually shall be in a range of 1 nm to 100 μm, is preferably in a range of 2 nm to 1,000 nm, is more preferably in a range of 5 nm to 500 nm, and is further preferably in a range of 20 nm to 200 nm.

When the organic film further contains a component except for the fused ring compound or the polymer thereof, the organic film preferably contains at least 30 mass % or more of either the fused ring compound or the polymer, and more preferably contains 50 mass % or more. If the content of either the fused ring compound or the polymer is less than 30 mass %, adequate electric-charge mobility tends to be hardly obtained.

The organic film may further contain, for instance, a compound having hole transport properties or electron transport properties so as to obtain excellent electric-charge (hole or electron) mobility. Examples of the compound having the hole transport properties can include a pyrazoline derivative, an arylamine derivative, a stilbene derivative, a triphenyl diamine derivative, an oligothiophene and a derivative thereof, a polyvinyl carbazole and a derivative thereof, polysilane and a derivative thereof, a polysiloxane derivative having an aromatic amine in a side chain or a main chain, polyaniline and a derivative thereof, polythiophene and a derivative thereof, polypyrrole and a derivative thereof, polyphenylene vinylene and a derivative thereof, and polythienylene vinylene and a derivative thereof.

In addition, examples of the compound having the electron transport properties can include an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyl dicyanoethylene and a derivative thereof, a diphenoquinone derivative, 8-hydroxyquinoline and a metal complex of a derivative thereof, polyquinoline and a derivative thereof, polyquinoxaline and a derivative thereof, polyfluorene and a derivative thereof, and fullerenes such as $C_{60}$ and a derivative thereof.

The organic film may further contain other components so as to enhance its characteristics. The other components include, for instance, a charge-generating material. The organic film contains the charge-generating material, thereby the thin film absorbs a light to generate an electric charge, and the organic film becomes suitable for such use applications like a photosensor as to need to generate the electric charge by absorbing the light.

The charge-generating material includes, for instance, an azo compound and a derivative thereof, a diazo compound and a derivative thereof, a non-metal phthalocyanine compound and a derivative thereof, a metal phthalocyanine compound and a derivative thereof, a perylene compound and a derivative thereof, a polycyclic quinone-based compound and a derivative thereof, a squarylium compound and a derivative thereof, an azulenium compound and a derivative thereof, a thiapyrylium compound and a derivative thereof, and fullerenes such as $C_{60}$ and a derivative thereof.

In addition, the organic film may further contain a sensitizer for sensitizing a function of generating the electric charge due to the above described charge-generating material, a stabilizer for stabilizing the thin film, a UV absorber for absorbing UV light, and the like.

Furthermore, the organic film may further contain a high-molecular compound other than the fused ring compound or the polymer as a polymer binder, from the viewpoint of enhancing its mechanical strength. Such a polymer binder preferably does not excessively lower electron transport properties, and preferably does not excessively absorb a visible light.

The polymer binder includes, for instance, poly(N-vinylcarbazole), polyaniline and a derivative thereof, polythiophene and a derivative thereof, poly(p-phenylene vinylene) and a derivative thereof, poly(2,5-thienylene vinylene) and a derivative thereof, polycarbonate, polyacrylate, polymethyl acrylate, polymethylmethacrylate, polystyrene, polyvinyl chloride and polysiloxane.

The above described organic film can be produced, for instance, by a method as will be described below.

Specifically, the organic film can be formed by applying a solution in which the fused ring compound and/or the polymer and the above described other components as needed have been dissolved in the solvent, onto a predetermined substrate, and removing the solvent by volatilization or the like.

The solvent can preferably dissolve or uniformly disperse the fused ring compound or the polymer, and the other components. Examples of such a solvent can include: an aromatic hydrocarbon-based solvent such as toluene, xylene, mesitylene, tetralin, decalin and n-butylbenzene; a halogenated saturated hydrocarbon-based solvent such as carbon tetrachloride, chloroform, dichloromethane, dichloroethane, chlorobutane, bromobutane, chloropentane, bromopentane, chlorohexane, bromohexane, chlorocyclohexane and bromocyclohexane; a halogenated aromatic hydrocarbon-based solvent such as chlorobenzene, dichlorobenzene and trichlorobenzene; and an ethers-based solvent such as tetrahydrofuran and tetrahydropyran. It is preferable that 0.1 mass % or more of the fused ring compound or the polymer is dissolved in a solvent.

Methods of applying the solution include, for instance, a spin coating method, a casting method, a microgravure coating method, a gravure coating method, a bar coating method, a roll coating method, a wire bar coating method, a dip coating method, a spray coating method, a screen printing method, a flexographic printing method, an offset printing method, an ink jet printing method and a dispenser printing method. Among them, the spin coating method, the flexographic printing method, the ink jet printing method or the dispenser printing method is preferable.

The organic film is obtained by the above described method, but the method for producing the organic film is not necessarily limited to the above described method. For instance, when a low-molecular material of the fused ring compound, an oligomer and the like is used as a raw material, a vapor deposition method such as a vacuum vapor deposition method can also be applied.

In addition, a step of orienting the fused ring compound or the polymer in the organic film may be further conducted for the organic film, according to the use application. By such orientation, the fused ring compound and the polymer (main chain or side chain) in the organic film result in being aligned in a fixed direction, and the charge transport properties of the organic film are further enhanced.

A method which is usually used for the orientation of a liquid crystal or the like can be applied to the method of orienting the organic film. Specifically, a rubbing method, a photo-orientation method, a shearing method (shear stress application method), a drawing-up application method and the like are preferable because of being simple and useful, and the rubbing method or the sharing method is more preferable.

[Organic Film Device]

The organic film of the above described embodiment results in having excellent charge (electron or hole) transport properties because of containing the fused ring compound and/or the polymer of the above described embodiment. Accordingly, this organic film can efficiently transport electrons or holes which have been injected from an electrode or the like, or electric charges which have been generated due to light absorption or the like, and can be applied to various electric devices (organic film device) with the use of the organic film. Examples of the organic film device will be each described below.

(Organic Film Transistor)

Firstly, the organic film transistor according to preferred embodiments will be described below. The organic film transistor may have a structure having a source electrode and a drain electrode, an organic film layer (active layer) which becomes a current path between the source electrode and the drain electrode and contains the fused ring compound and/or the polymer of the present invention, and a gate electrode which controls current quantity passing through the current path, and the examples include an electric-field effect type and an electrostatic induction type.

The electric-field effect type organic film transistor preferably has a source electrode and a drain electrode, an organic film layer (active layer) which becomes a current path between the source electrode and the drain electrode and contains the fused ring compound and/or the polymer of the present invention, a gate electrode which controls the current quantity passing through the current path, and an insulation layer arranged between the active layer and the gate electrode. It is particularly preferable that the source electrode and the drain electrode are provided in contact with the organic film layer (active layer) containing the fused ring compound and/or the polymer of the present invention, and that the gate electrode is further provided so as to sandwich the insulation layer which comes in contact with the organic film layer.

On the other hand, it is preferable that the electrostatic induction type organic film transistor has a source electrode and a drain electrode, an organic film layer which becomes a current path between the source electrode and the drain electrode and contains the fused ring compound and/or the polymer of the present invention and a gate electrode which controls the current quantity passing through the current path, and that the gate electrode is preferably provided in the organic film layer. It is particularly preferable that the source electrode, the drain electrode and the gate electrode provided in the organic film layer are provided in contact with the organic film layer containing the fused ring compound and/or the polymer of the present invention. The gate electrode may have a structure in which a current path through which an electric current passes from the source electrode to the drain electrode is formed and the quantity of the electric current that passes through the current path can be controlled by voltage applied to the gate electrode, and includes a comb-shaped electrode, for instance.

FIG. 1 is a schematic sectional view of an organic film transistor (electric-field effect type organic film transistor) according to a first embodiment. The organic film transistor 100 illustrated in FIG. 1 includes: a substrate 1; a source electrode 5 and a drain electrode 6 formed on the substrate 1 so as to have a predetermined space; an active layer 2 formed on the substrate 1 so as to cover the source electrode 5 and the drain electrode 6; an insulation layer 3 formed on the active layer 2; and a gate electrode 4 formed on the insulation layer 3 so as to cover a region of the insulation layer 3 between the source electrode 5 and the drain electrode 6.

Figure 2:
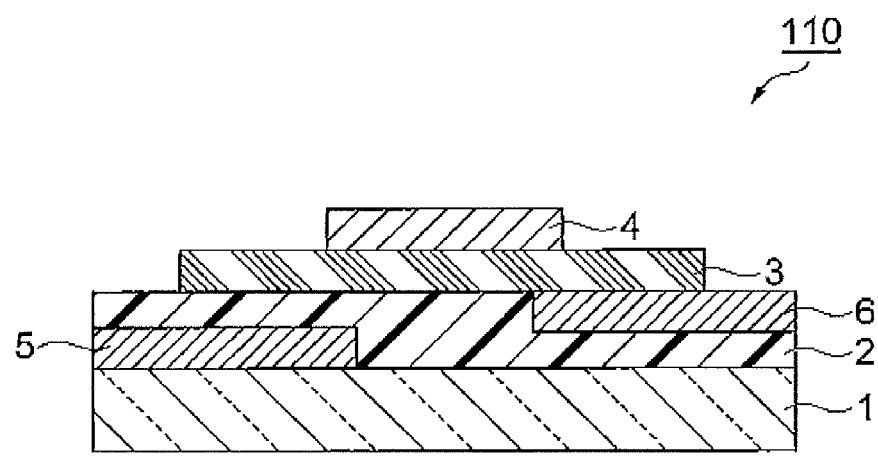
FIG. 2 is a schematic sectional view of an organic film transistor according to a second embodiment.

FIG. 2 is a schematic sectional view of an organic film transistor (electric-field effect type organic film transistor) according to a second embodiment. The organic film transistor 110 illustrated in FIG. 2 includes: a substrate 1; a source electrode 5 formed on the substrate 1; an active layer 2 formed on the substrate 1 so as to cover the source electrode 5; a drain electrode 6 formed on the active layer 2 so as to have a predetermined space to the source electrode 5; an insulation layer 3 formed on the active layer 2 and the drain electrode 6; and a gate electrode 4 formed on the insulation layer 3 so as to cover a region of the insulation layer 3 between the source electrode 5 and the drain electrode 6.

Figure 3:
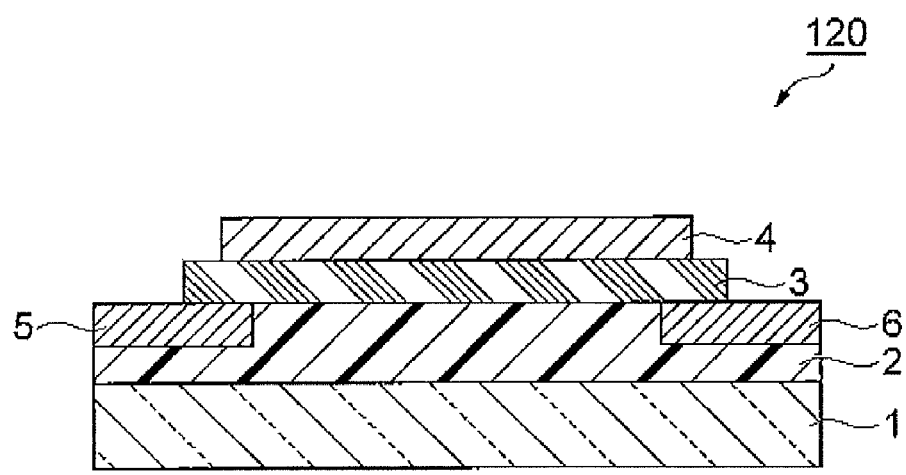
FIG. 3 is a schematic sectional view of an organic film transistor according to a third embodiment.

FIG. 3 is a schematic sectional view of an organic film transistor (electric-field effect type organic film transistor) according to a third embodiment. The organic film transistor 120 illustrated in FIG. 3 includes: a substrate 1; an active layer 2 formed on the substrate 1; a source electrode 5 and a drain electrode 6 formed on the active layer 2 so as to have a predetermined space; an insulation layer 3 formed on the active layer 2 so as to partially cover the source electrode 5 and the drain electrode 6; and a gate electrode 4 formed on the insulation layer 3 so as to partially cover each of a region of the insulation layer 3 having the source electrode 5 formed in its lower part and a region of the insulation layer 3 having the drain electrode 6 formed in its lower part.

Figure 4:
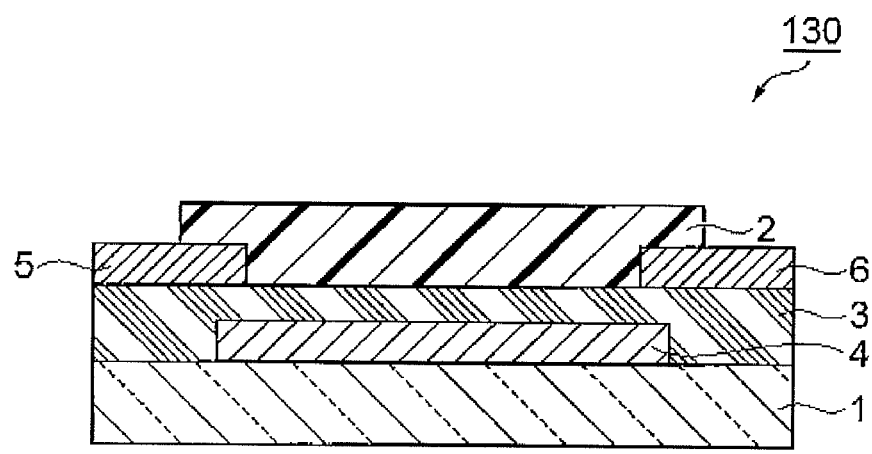
FIG. 4 is a schematic sectional view of an organic film transistor according to a fourth embodiment.

FIG. 4 is a schematic sectional view of an organic film transistor (electric-field effect type organic film transistor) according to a fourth embodiment. The organic film transistor 130 illustrated in FIG. 4 includes: a substrate 1; a gate electrode 4 formed on the substrate 1; an insulation layer 3 formed on the substrate 1 so as to cover the gate electrode 4; a source electrode 5 and a drain electrode 6 formed on the insulation layer 3 at a predetermined space so as to partially cover a region of the insulation layer 3 having the gate electrode 4 formed in its lower part; and an active layer 2 formed on the insulation layer 3 so as to partially cover the source electrode 5 and the drain electrode 6.

Figure 5:
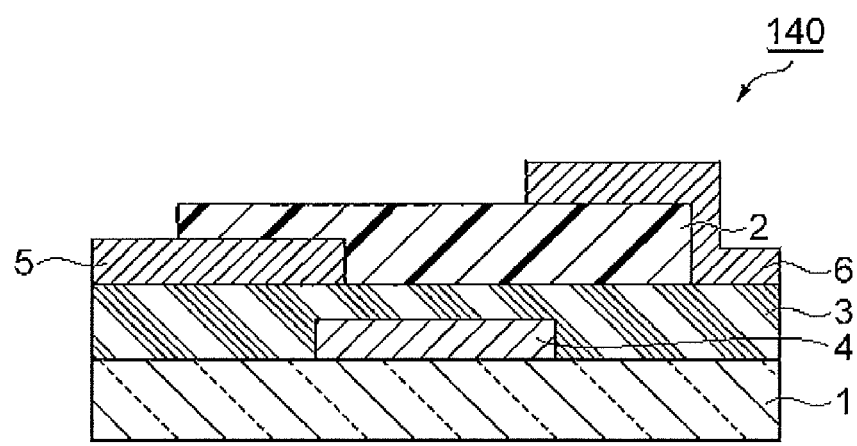
FIG. 5 is a schematic sectional view of an organic film transistor according to a fifth embodiment.

FIG. 5 is a schematic sectional view of an organic film transistor (electric-field effect type organic film transistor) according to a fifth embodiment. The organic film transistor 140 illustrated in FIG. 5 includes: a substrate 1; a gate electrode 4 formed on the substrate 1; an insulation layer 3 formed on the substrate 1 so as to cover the gate electrode 4; a source electrode 5 formed on the insulation layer 3 so as to partially cover a region of the insulation layer 3 having the gate electrode 4 formed in its lower part; an active layer 2 formed on the insulation layer 3 so as to partially cover the source electrode 5; and a drain electrode 6 formed on the insulation layer 3 so as to partially cover a region of the active layer 2 having the gate electrode 4 formed in its lower part and have a predetermined space to the source electrode 5.

Figure 6:
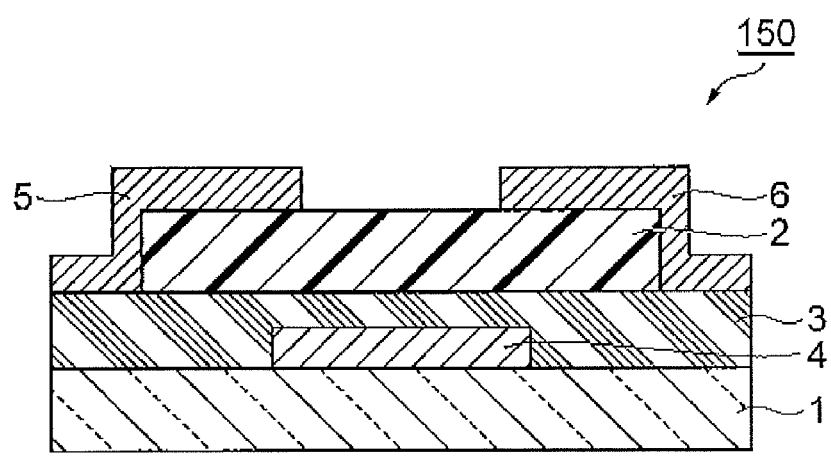
FIG. 6 is a schematic sectional view of an organic film transistor according to a sixth embodiment.

FIG. 6 is a schematic sectional view of an organic film transistor (electric-field effect type organic film transistor) according to a sixth embodiment. The organic film transistor 150 illustrated in FIG. 6 includes: a substrate 1; a gate electrode 4 formed on the substrate 1; an insulation layer 3 formed on the substrate 1 so as to cover the gate electrode 4; an active layer 2 formed so as to cover a region of the insulation layer 3 having the gate electrode 4 formed in its lower part; a source electrode 5 formed on the insulation layer 3 so as to partially cover a region of the active layer 2 having the gate electrode 4 formed in its lower part; and a drain electrode 6 formed on the insulation layer 3 so as to have a predetermined space to the source electrode 5 and partially cover a region of the active layer 2 having the gate electrode 4 formed in its lower part.

Figure 7:
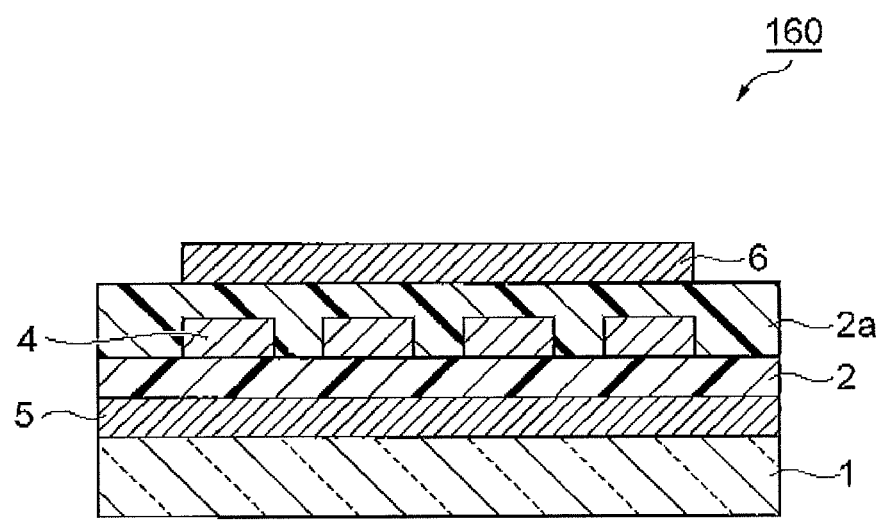
FIG. 7 is a schematic sectional view of an organic film transistor according to a seventh embodiment.

FIG. 7 is a schematic sectional view of an organic film transistor (electrostatic induction type organic film transistor) according to a seventh embodiment. The organic film transistor 160 illustrated in FIG. 7 includes: a substrate 1; a source electrode 5 formed on the substrate 1; an active layer 2 formed on the source electrode 5; a plurality of gate electrodes 4 formed on the active layer 2 so as to have a predetermined space; an active layer 2a (where the material constituting the active layer 2a may be the same as or different from that of the active layer 2) formed on the active layer 2 so as to cover the whole of the gate electrode 4; and a drain electrode 6 formed on the active layer 2a.

In the organic film transistor according to the first to the seventh embodiments, the active layer 2 and/or the active layer 2a contain the fused ring compound and/or the polymer of the present invention, and become a current path (channel) between the source electrode 5 and the drain electrode 6. The gate electrode 4 controls the current quantity passing through the current path (channel) in the active layer 2 and/or the active layer 2a by the application of voltage.

Such an electric-field effect type organic film transistor can be produced with a well-known method, for instance, a method described in Japanese Patent Application Laid-Open Publication No. 5-110069. An electrostatic induction type organic film transistor can be produced with a well-known method, for instance, a method described in Japanese Patent Application Laid-Open Publication No. 2004-006476.

The substrate 1 is not particularly limited as long as the substrate does not obstruct characteristics of the organic film transistor, but can employ a glass substrate, a flexible film substrate and a plastic substrate.

It is extremely advantageous and preferable in production to use an organic-solvent-soluble compound when forming the active layer 2, and accordingly, the organic film to be active layer 2 can be formed by using a method described above for producing the organic film of the present invention.

A material of the insulation layer 3 contacting the active layer 2 is not particularly limited as long as the material has high electric insulation properties, and can employ a well-known material. The material of the insulation layer 3 includes, for instance, SiOx, SiNx, $Ta_2O_5$, polyimide, polyvinyl alcohol, polyvinyl phenol, organic glass and a photoresist. A material having a high dielectric constant is more preferable from the viewpoint of lowering voltage.

When forming the active layer 2 on the insulation layer 3, it is also possible to modify the surface of the insulation layer 3 by treating the surface the insulation layer 3 with a surface treatment agent such as a silane coupling agent and then Balm the active layer 2, in order to enhance interfacial characteristics between the insulation layer 3 and the active layer 2. The surface treatment agent includes, for instance, long-chain alkyl chlorosilanes, long-chain alkyl alkoxy silanes, fluorination alkyl chlorosilanes, fluorinated alkyl alkoxy silanes, and a silyl amine compound such as hexamethyldisilazane. It is also possible to treat the surface of the insulation layer with ozone UV or $O_2$ plasma before treating the surface with the surface treatment agent.

In addition, it is preferable to form a protective film on the organic film transistor in order to protect the device after having produced the organic film transistor. Thereby, the organic film transistor is blocked from the atmosphere, which can suppress the degradation of the characteristics of the organic film transistor. In addition, the protective film can decrease the influence to be exerted from the step of forming the display device to be driven on the organic film transistor.

The method for forming the protective film includes, for instance, a method of covering the device with a UV curable resin, a thermoset resin or an inorganic $SiON_x$ film. It is preferable for effectively blocking the device from the atmosphere to conduct a step until forming the protective film after having produced the organic film transistor, without exposing the device to the atmosphere (in dried nitrogen atmosphere or in the vacuum, for instance).

(Solar Cell)

Figure 8:
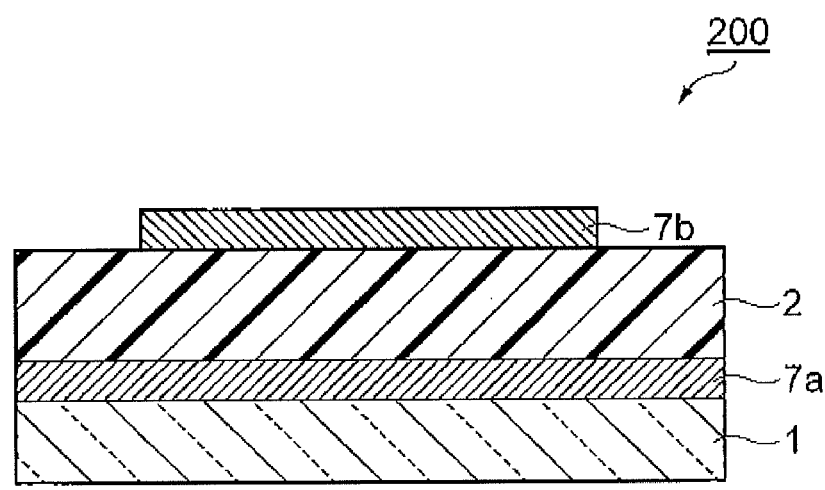
FIG. 8 is a schematic sectional view of a solar cell according to an embodiment.

Next, the application of the organic film of the present invention to a solar cell will be described below. FIG. 8 is a schematic sectional view of the solar cell according to an embodiment. The solar cell 200 illustrated in FIG. 8 includes: a substrate 1; a first electrode 7a formed on the substrate 1; an active layer 2 which is formed of an organic film containing the fused ring compound and/or the polymer of the present invention is formed on the first electrode 7a; and a second electrode 7b formed on the active layer 2.

The solar cell according to the present embodiment uses a transparent or semi-transparent electrode in one of the first electrode 7a and the second electrode 7b. The electrode material can use a metal such as aluminum, gold, silver, copper, an alkaline metal and an alkaline-earth metal, or a semi-transparent film and a transparent electroconductive film thereof. In order to obtain a high open voltage, it is preferable that each of the electrodes is selected so as to have a large difference between the work functions. The active layer 2 (organic film) can employ a charge-generating agent, a sensitizer and the like which are added, in order to enhance the light sensitivity. For a substrate 1, a silicon substrate, a glass substrate, a plastic substrate or the like can be used.

(Photosensor)

Figure 9:
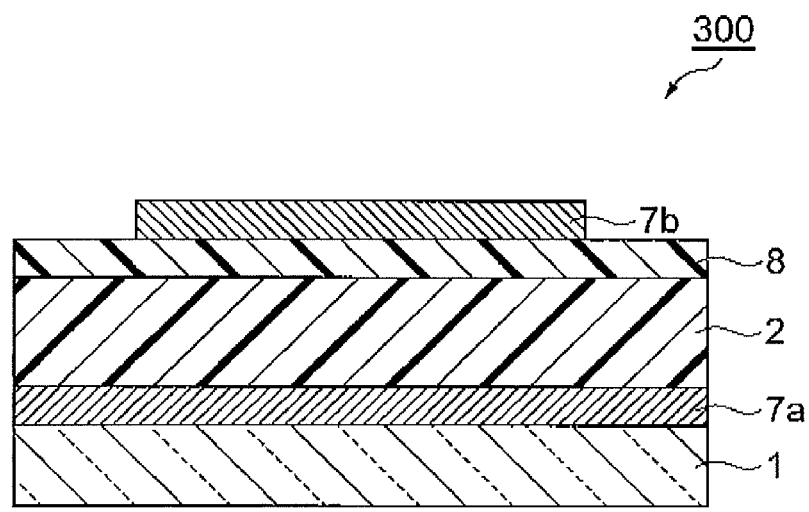
FIG. 9 is a schematic sectional view of a photosensor according to a first embodiment.

Next, the application of the organic film of the present invention to a photosensor will be described below. FIG. 9 is a schematic sectional view of a photosensor according to a first embodiment. The photosensor 300 illustrated in FIG. 9 includes: a substrate 1; a first electrode 7a formed on the substrate 1; an active layer 2 which is formed of an organic film containing the fused ring compound and/or the polymer of the present invention and is formed on the first electrode 7a; a charge-generating layer 8 formed on the active layer 2; and a second electrode 7b formed on the charge-generating layer 8.

Figure 10:
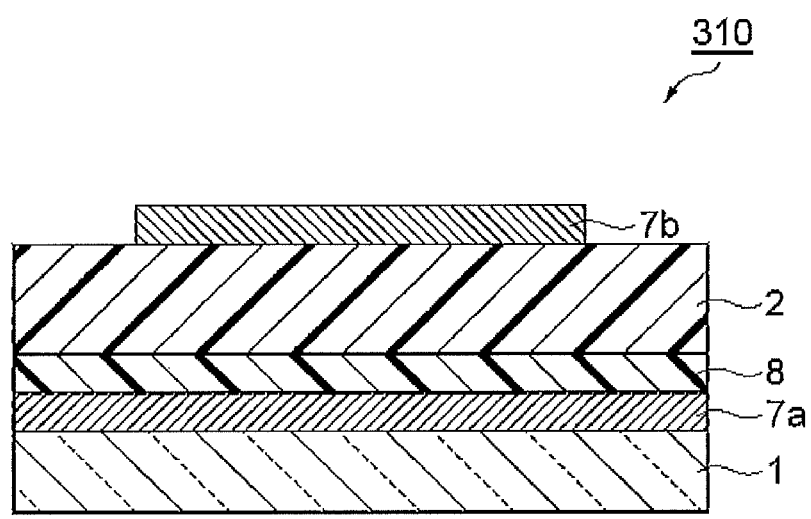
FIG. 10 is a schematic sectional view of a photosensor according to a second embodiment.

FIG. 10 is a schematic sectional view of a photosensor according to a second embodiment. The photosensor 310 illustrated in FIG. 10 includes: a substrate 1; a first electrode 7a formed on the substrate 1; a charge-generating layer 8 formed on the first electrode 7a; an active layer 2 which is formed of an organic film containing the fused ring compound and/or the polymer of the present invention and is formed on the charge-generating layer 8; and a second electrode 7b formed on the active layer 2.

Figure 11:
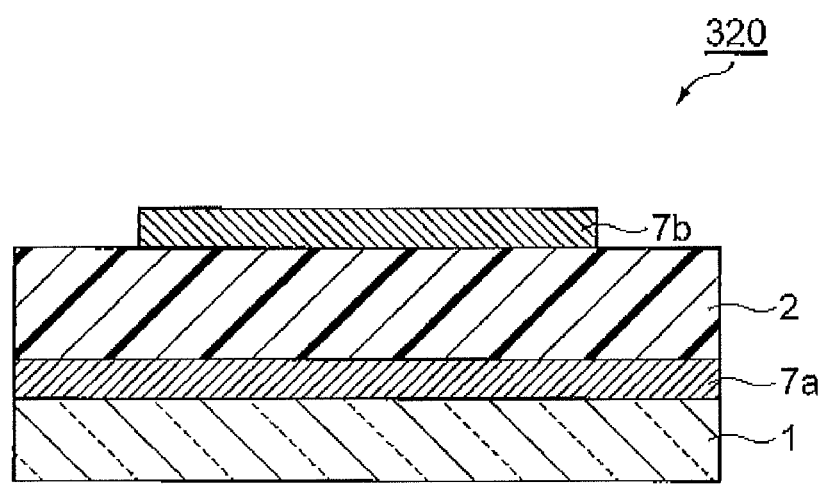
FIG. 11 is a schematic sectional view of a photosensor according to a third embodiment.

FIG. 11 is a schematic sectional view of a photosensor according to a third embodiment. The photosensor 320 illustrated in FIG. 11 includes: a substrate 1; a first electrode 7a formed on the substrate 1; an active layer 2 which is formed of an organic film containing the fused ring compound and/or the polymer of the present invention and is formed on the first electrode 7a; and a second electrode 7b formed on the active layer 2.

In the photosensor according to the first to third embodiments, a transparent or semi-transparent electrode is used for one of the first electrode 7a and the second electrode 7b. The charge-generating layer 8 is a layer which absorbs light to generate an electric charge. The electrode material can use a metal such as aluminum, gold, silver, copper, an alkaline metal and an alkaline-earth metal, or a semi-transparent film and a transparent electroconductive film thereof. The active layer 2 (organic film) can employ a carrier-generating agent, a sensitizer and the like which are added, in order to enhance the light sensitivity. For a substrate 1, a silicon substrate, a glass substrate, a plastic substrate or the like can be used.

In the above, the present invention has been described in detail with reference to the embodiments, but the present invention is not limited to the above described embodiments, and can be modified in various ways, in such a range as not to apart from the scope of the present invention. For instance, the organic film device is not limited to the above described embodiment as long as the organic film device is an electric device to which the organic film is applied. The organic film device other than the above description includes, for instance, an organic EL device, an organic memory, a photorefractive device, a spatial light modulator and an imaging device.

EXAMPLES

The present invention will be described further in detail below with reference to examples, but the present invention is not limited to these examples.

(Measurement Condition)

In the following synthesis examples and examples, various analyses or the like was conducted on the following condition. Specifically, a nuclear magnetic resonance (NMR) spectrum was measured with JNM-GSX-400 made by JEOL Ltd. A gas chromatography mass spectrometry (GC-MS) was conducted with an electron bombardment method while using QP-5050 made by Shimadzu Corporation. The high-resolution mass spectrometry (HRMS) was conducted with JMS-DX-303 made by JEOL Ltd. As for the gas chromatograph (GC) analysis, GC-8A made by Shimadzu Corporation was used, on which a glass column (inner diameter of 2.6 mm and length of 1.5 m) filled with silicon OV-17 made by GL Sciences, Inc. was mounted. Wakogel C-200 made by Wako Pure Chemical Industries, Ltd. was used for a silica gel in column chromatographic separation.

Referential Example 1 of Synthesis

Synthesis of 3,3'-diiodo-2,2'-bibenzo[b]thiophene

Firstly, 3,3'-dibromo-2,2'-bibenzo[b]thiophene of a starting raw material was synthesized with reference to the description in a reference literature (U. Dahlmann, R. Neidlein, Helv. Chim. Acta., 1997, 80, 111-120). Then, a halogen exchange reaction was conducted by using the 3,3'-dibromo-2,2'-bibenzo[b]thiophene to synthesize 3,3'-diiodo-2,2'-bibenzo[b]thiophene.

Specifically, firstly, 3,3'-dibromo-2,2'-bibenzo[b]thiophene (2.89 g, 6.7 mmol) was charged into a 500 mL three-neck flask, and the inside of a reaction vessel was replaced with nitrogen. Diethyl ether (160 mL) was added into the flask, was stirred and was cooled to −78° C. Subsequently, n-BuLi (1.6 M hexane solution, 8.90 mL, 14.5 mmol) was added, and was stirred for 1 hour. Furthermore, iodine (3.41 g, 13.4 mmol) was added, and the mixture was stirred for 2 hours under room temperature to be reacted.

Then, a supernatant liquid of a reaction mixture was collected by decantation, a remaining solid was dissolved into $CH_2Cl_2$ and washed with a saturated sodium thiosulfate aqueous solution together with the supernatant liquid. After an organic layer was dried with sodium sulfate, the product was filtered through a filter paper. Then, 3,3'-diiodo-2,2'-bibenzo[b]thiophene of a target object was obtained as a state of a white solid (2.76 g, yield of 79%) by distilling a solvent off from a filtrate and recrystallizing the obtained solid with toluene. As a result of having had measured the melting point of the obtained white solid, the melting point was 194° C.

The result of measured $^1$H-NMR and HRMS of the obtained target object was as described below.

$^1$H-NMR (400 MHz, CDCl$_3$) δ 7.92-7.78 (m, 4H), 7.57-7.43 (m, 4H); HRMS (EI): m/z=517.8164 (Calcd. For C$_{16}$H$_8$I$_2$S$_2$: 517.8157)

Manufacture of Fused Ring Compound

Example 1

Synthesis of (5,6-di(n-heptyl)benzo[2,1-b:3,4-b']bis[1]benzothiophene

Into a 30 mL two-neck flask, 3,3'-diiodo-2,2'-bibenzo[b]thiophene (575 mg, 1.11 mmol) obtained in the above description, 8-hexadecyne (302 mg, 1.33 mmol), palladium acetate (24.4 mg, 0.11 mmol), N,N-dicyclohexyl methylamine (520 mg, 2.66 mmol) and DMF (15 mL) were charged, the inside of a reaction vessel was replaced with nitrogen, and the mixture was heated and stirred at 140° C. for 2.5 hours to be reacted.

After the reaction, CH$_2$Cl$_2$ and dilute hydrochloric acid were added to the product, the product was extracted, an organic layer was dried with sodium sulfate and the product was then filtered through a filter paper. 5,6-di(n-heptyl)benzo[2,1-b:3,4-b'] bis[1]benzothiophene of a target object was obtained in a state of a yellow solid (470 mg, yield of 87%), by distilling a solvent off from a filtrate, dissolving a remaining solid into toluene, and refining the solution with silica gel column chromatography which used hexane as a developing solvent. As a result of having had measured the melting point of the obtained solid, the melting point was 103° C.

The result of measured $^1$H-NMR and HRMS of the obtained target object was as described below.

$^1$H-NMR (400 MHz, CDCl$_3$); δ 8.31 (d, J=7.6 Hz, 2H), 7.90 (d, J=7.6, 2H), 7.55-7.41 (m, 4H), 3.43-3.30 (m, 4H), 1.88-1.73 (m, 4H), 1.70-1.57 (m, 4H), 1.55-1.30 (m, 12H), 0.92 (t, J=7.3 Hz, 6H), FIRMS (EI): m/z=486.2421 (Calcd. For C$_{32}$H$_{38}$S$_2$: 486.2415)

Example 2

Synthesis of 2,9-dibromo-5,6-di(n-decanyl)benzo[2,1-b:3,4-b']bis[1]benzothiophene In to a two-neck flask, 6,6'-dibromo-3,3'-diiodo-2,2'-bibenzo[b]thiophene, 1,2-didecanyl ethyne, palladium acetate, N,N-dicyclohexyl methylamine and DMF are charged, the inside of a reaction vessel is replaced with nitrogen, and the mixture is heated and stirred to be reacted.

After the reaction, CH$_2$Cl$_2$ and dilute hydrochloric acid are added to the product, the product is extracted, an organic layer is dried with sodium sulfate and the product is then filtered through a filter paper. 2,9-dibromo-5,6-di(n-heptyl)benzo[2,1-b:3,4-b']bis[1]benzothiophene of a target object is obtained in a state of a yellow solid, by distilling a solvent off from a filtrate, dissolving a remaining solid into toluene, and refining the solution with silica gel column chromatography which uses hexane as a developing solvent.

Production of Polymer

Example 3

Synthesis of poly(5,6-di(n-decanyl)benzo[2,1-b:3,4-b']bis[1]benzothiophene)

In to a two-neck flask, 2,9-dibromo-5,6-di(n-heptyl)benzo[2,1-b:3,4-b']bis[1]benzothiophene, Ni(COD)$_2$, 1,5-cyclooctadiene, bipyridyl and N,N-dimethylformamide are charged, the inside of a reaction vessel is replaced with nitrogen, and the mixture is stirred at 60° C. to be reacted.

Toluene is added to the solution which has finished the reaction, and the product is washed with water. Subsequently, an organic layer is dried with sodium sulfate. Then, poly(5,6-di(n-decanyl)benzo[2,1-b:3,4-b']bis[1]benzothiophene) of a target object is obtained in a state of a dark brown solid, by distilling a solvent off from a filtrate after filtration, refining the solution with silica gel column chromatography which uses hexane and toluene as a developing solvent, and adding ethanol to the obtained liquid. The obtained polymer shall be a polymer A.

Production and Evaluation of an Organic Film Device

Example 4

Production of Organic Film Transistor and Evaluation of its Characteristics

The appropriate amount of the polymer A is weighed, and chloroform is added thereto to prepare a chloroform solution; the solution is filtered through a membrane filter made of Teflon (registered trademark) to form an application solution.

Next, a substrate is prepared by forming an oxide film of thermally oxidized silicon, which will act as an insulating layer, on the surface of a heavily doped n-type silicon substrate which will act as a gate electrode, is subjected to ultrasonic cleaning with an alkali detergent, ultrapure water and acetone, and then the surface is cleaned by ozone UV irradiation. Hexamethyldisilazane (HMDS, produced by Sigma-Aldrich corporation) is added dropwise onto this cleaned substrate, which is then spun to treat the substrate surface with HMDS. The above described chloroform solution of the polymer A (application solution) is added dropwise onto this surface-treated substrate, which is then spun to form a thin film of the polymer A thereon.

Then, on the thin film of the polymer A, a Pt/Au electrode is vapor-deposited with a vacuum deposition method by using a metal mask, a source electrode and a drain electrode are formed, and an organic film transistor is obtained.

When the transistor characteristics of the obtained organic film transistor are measured by changing the gate voltage $V_G$ and the voltage $V_{SD}$ between the source and the drain in a vacuum, adequate Id-Vg characteristics are obtained.

The invention claimed is:

1. A fused ring compound represented by the following formula (1):

[Chemical Formula 1]

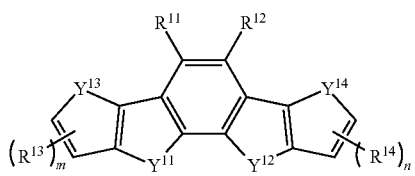
(1)

wherein $R^{11}$ and $R^{12}$ each independently represent a hydrogen atom, an alkyl group, an alkoxy group, an alkylthio group, an alkylamino group, an alkoxycarbonyl group having 3 or more carbon atoms in the alkyl moiety thereof, an aryl group that may have a substituent, a monovalent heterocyclic group that may have a substituent, or a cyano group, wherein at least one of $R^{11}$ and $R^{12}$ is not a hydrogen atom; $R^{13}$ and $R^{14}$ each independently represent a monovalent group and m and n each independently are an integer of 0 to 2, when there are a plurality of $R^{13}$s and a plurality of $R^{14}$s, the $R^{13}$s may be the same as or different from each other and the $R^{14}$s may be the same as or different from each other; $Y^{11}$ and $Y^{12}$ are a divalent group represented by the following formula (2a); and $Y^{13}$ and $Y^{14}$ are each independently a divalent group represented by the following formula (2a), (2b), (2c), (2d), (2e), (2f), (2g), (2h) or (2i):

[Chemical Formula 2]

 (2a)

 (2b)

 (2c)

 (2d)

 (2e)

 (2f)

 (2g)

 (2h)

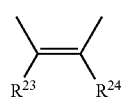 (2i)

wherein $R^{21}$, $R^{22}$, $R^{23}$ and $R^{24}$ each independently represent a hydrogen atom or a monovalent group; and $R^{23}$ and $R^{24}$ may be bonded together to form a ring.

2. The fused ring compound according to claim 1, wherein the $Y^{11}$ and the $Y^{12}$ are a divalent group represented by formula (2a), and the $Y^{13}$ and the $Y^{14}$ are a divalent group represented by formula (2i).

3. The fused ring compound according to claim 1, wherein the $R^{11}$ and the $R^{12}$ each independently represent an alkyl group that has 1 to 10 carbon atoms or an aryl group that has 6 to 20 carbon atoms and may have a substituent.

4. A method for producing a fused ring compound comprising making a compound represented by the following formula (8a) react with a compound expressed by the following formula (8b) in the presence of a base and a metal complex catalyst to obtain a fused ring compound represented by the following formula (8c):

[Chemical Formula 8]

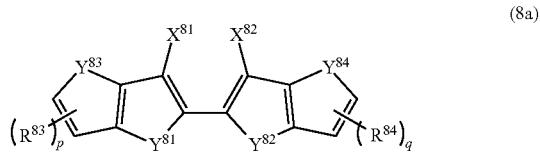 (8a)

 (8b)

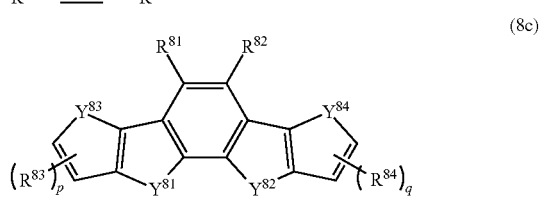 (8c)

wherein $X^{81}$ and $X^{82}$ each independently represent a hydrogen atom or a halogen atom, wherein at least one of $X^{81}$ and $X^{82}$ is a halogen atom; $R^{81}$ and $R^{82}$ each independently represent a hydrogen atom, an alkyl group, an alkoxy group, an alkylthio group, an alkylamino group, an alkoxycarbonyl group having 3 or more carbon atoms in the alkyl moiety thereof, an aryl group that may have a substituent, a monovalent heterocyclic group that may have a substituent, or a cyano group, wherein at least one of $R^{81}$ and $R^{82}$ is not a hydrogen atom; $R^{83}$ and $R^{84}$ each independently represent a monovalent group and p and q are each independently an integer of 0 to 2, when there are a plurality of $R^{83}$s and a plurality of $R^{84}$s, the $R^{83}$s may be the same as or different from each other and the $R^{84}$s may be the same as or different from each other; $Y^{81}$ and $Y^{82}$ represent a divalent group represented by the following formula (9a); and $Y^{83}$ and $Y^{84}$ each independently represent a divalent group represented by the following formula (9a), (9b), (9c), (9d), (9e), (9f), (9g), (9h) or (9i):

[Chemical Formula 9]

 (9a)

 (9b)

 (9c)

-continued

 (9d)

 (9e)

 (9f)

 (9g)

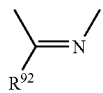 (9h)

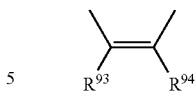 (9i)

wherein $R^{91}$, $R^{92}$, $R^{93}$ and $R^{94}$ each independently represent a hydrogen atom or a monovalent group; and $R^{93}$ and $R^{94}$ may be bonded together to form a ring.

5. The method for producing a fused ring compound according to claim 4, wherein the $Y^{81}$ and the $Y^{82}$ are a divalent group represented by formula (9a), and the $Y^{83}$ and the $Y^{84}$ are a divalent group represented by formula (9i).

6. The method for producing a fused ring compound according to claim 4, wherein at least one of the $X^{81}$ and the $X^{82}$ is an iodine atom.

7. An organic film comprising the fused ring compound according to claim 1.

8. An organic film device comprising the organic film according to claim 7.

9. An organic film transistor comprising the organic film according to claim 7.

* * * * *